United States Patent
Hatab

(10) Patent No.: US 6,658,144 B1
(45) Date of Patent: *Dec. 2, 2003

(54) DIFFRACTION TOMOGRAPHY FOR MONITORING LATENT IMAGE FORMATION

(75) Inventor: Ziad R. Hatab, Boise, ID (US)

(73) Assignee: Micron Technology, Inc., Boise, ID (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,447

(22) Filed: May 22, 1998

Related U.S. Application Data

(60) Provisional application No. 60/047,530, filed on May 23, 1997.

(51) Int. Cl.[7] .............................. G06K 9/46; G06T 7/60
(52) U.S. Cl. ........................ 382/144; 108/131; 108/145; 108/280; 438/16; 356/128
(58) Field of Search .................................. 382/108, 131, 382/144, 280, 286, 318, 145; 702/40, 77, 159; 438/7, 8, 16; 430/30, 290; 250/559.44, 559.46, 390.09; 356/237.4, 237.5, 305, 337–343, 128, 237.1; 324/76, 37; 359/563, 123; 378/70, 4, 21, 76

(56) References Cited

U.S. PATENT DOCUMENTS

| | | | | |
|---|---|---|---|---|
| 4,188,123 A | * | 2/1980 | Kleinknecht | 356/354 |
| 4,408,884 A | * | 10/1983 | Kleinknecht et al. | 356/355 |
| 4,968,108 A | * | 11/1990 | Ikeda et al. | 350/3.7 |
| 5,288,572 A | * | 2/1994 | Giapis et al. | 430/30 |
| 5,420,680 A | * | 5/1995 | Isobe et al. | 356/128 |
| 5,594,549 A | * | 1/1997 | Mori et al. | 356/401 |
| 5,674,652 A | * | 10/1997 | Bishop et al. | 430/30 |
| 5,703,692 A | * | 12/1997 | McNeil et al. | 356/445 |
| 5,714,750 A | * | 2/1998 | Eastman et al. | 235/462 |
| 5,830,611 A | * | 11/1998 | Bishop et al. | 430/30 |
| 5,963,315 A | * | 10/1999 | Hiatt et al. | 356/237.3 |
| 5,968,691 A | * | 10/1999 | Yoshioka et al. | 430/30 |
| 5,988,502 A | * | 11/1999 | Krichever et al. | 235/454 |
| 6,005,916 A | * | 12/1999 | Johnson et al. | 378/87 |

OTHER PUBLICATIONS

Werner J. Glantsching, How Accurately can one Reconstruct an Index Profile from Transverse Measurement Data, IEEE Journal of Lightwave Technology, vol. LT–3, No. 3, Jun. 1995, pp. 678–683.*

Murnane et al., Developed Photoresist Metrology using Scatterometry, Proc. SPIE vol. 2196, p. 47–59, May, 1994.*

Torolf C. Wedberg et al., Quantitative Microscopy of Phase Objects by Optical Diffraction Tomography, Proc. SPIE vol. 2083, p. 168–173, Feb. 1994.*

Sabatier, P.C., et al., *Basic Methods of Tomography and Inverse Problems*, Adam Hilger, Bristol, pp. 125–467, (1987).

(List continued on next page.)

*Primary Examiner*—Brian Werner
(74) *Attorney, Agent, or Firm*—Schwegman, Lundberg, Woessner & Kluth, P.A.

(57) ABSTRACT

A system and method of reconstructing an image of a structure having periodic variations in index of refraction. Electromagnetic waves are projected onto the structure and the resulting diffracted electromagnetic waves are measured, wherein the step of measuring includes the step of determining a plurality of intensities DE. Refractive terms can then be calculated as a function of the intensities DE.

31 Claims, 9 Drawing Sheets

OTHER PUBLICATIONS

Adams, T.E., "Applications of Latent Image Metrology in Microlithography", *SPIE, 1464*, pp. 294–312, (1991).

Bagchi, S., et al., "The nonuniform discrete fourier transform and its applications in filter design: Part I—1–D", *IEEE*, pp. 422–433, (Jun. 1996).

Baltes, H.P., et al., "Coherent and incoherent grating reconstruction", *J. Opt. Soc. Am. A, 3(8)*, pp. 1268–1275, (Aug. 1986).

Baumbach, G.T., et al., "X–ray diffraction from epitaxial multilayered surface gratings", *J. Phys. D: Appl. Phys., 28*, pp. 2321–2327, (1995).

Bergossi, O., et al., "Visualization of latent images by reflection near field optical microscopy", *Ultramicroscopy, 61*, pp. 241–246, (1995).

Botten, L.C., "A new formalism for transmission gratings", *Optica Acta, 25(6)*, pp. 481–499, (1978).

Bouzid, A., et al., "Scattering analysis of slanted fiber gratings", *Applied Optics, 36(3)*, pp. 558–562, (Jan. 1997).

Box,, G.P., et al., "An Analysis of Transformation, 26(1)", *Journal of the Royal Statistical Society, 26(1)*, pp. 211–252, (1964).

Burov, V.A., et al., "Diffraction tomography as an inverse scattering problem: the interpolation approach (linearized version)", *Sov. Phys. Acoust., 38(4)*, pp. 349–355, (1992).

Carter, W.H., "On some diffraction effiency equations for a thick grating or hologram", *Optics Communications, 103*, pp. 1–7, (1993).

Devaney, A.J., "A Computer Simulation Study of Diffraction Tomography", *IEEE Transactions on Biomedical Engineering, BME–30(7)*, pp. 377–386, (1983).

Devaney, A.J., "A Filtered Backpropagation Algorithm for Diffraction Tomography", *Ultrasonic Imaging, 4*, pp. 336–350, (1982).

Devaney, A.J., "Geophysical Diffraction Tomography", *IEEE*, pp. 3–13, (Jan. 1984).

Devaney, A.J., "Inverse scattering theory foundations of tomography with diffracting wavefields", *SPIE, 768, International Symposium on Pattern Recognition and Acoustical Imaging*, pp. 2–6, (1987).

Devaney, A.J., "Nonuniqueness in the inverse scattering problem", *J. Math. Phys., 19(7)*, pp. 1526–1531, (Jul. 1978).

Fadda, E., et al., "Characterization of latent image by surface energy determined by contact angle measurements", *Journal of Vacuum Science and Technology B, 13(3)*, pp. 1055–1057, (1995).

Fowles, G.R., *Introduction to Modern Optics*, Dover Publications Inc., New York, pp. 21–84, (1975).

Frolik, J.L., et al., "An Asymmetric Discrete–Time Approach for the Design and Analysis of Periodic Waveguide Gratings", *Journal of Lightwave Technology, 13(2)*, pp. 175–185, (1995).

Garcia, N., et al., "Near–field optics inverse–scattering reconstruction of reflective surfaces", *Optics Letters, 18924)*, pp. 2090–2092, (1993).

Gaylord, T.K., et al., "Analysis and Applications of Optical Diffraction by Gratings", *Proceedings of the IEEE, 73(5)*, pp. 894–937, (May 1985).

Ghandi, S.K., *VLSI Fabrication Principles*, John Wiley & Sons Inc., New York, pp. 533–566, (1983).

Glytsis, E.N., et al., "Rigorous 3–D coupled wave diffraction analysis of multiple superposed gratings in anisotropic media", *Applied Optics, 28(12)*, pp. 2401–2421, (Jun. 1989).

Goodman, J.W., *Introduction to Fourier Optics*, McGraw–Hill, San Francisco, pp. 57–75, (1968).

Gregus, J.A., et al., "Real–time latent image monitoring during holographic fabrication of submicron diffraction gratings", *J. Vac. Sci. Technol. B, 11(6)*, pp. 2468–2472, (1993).

Gretzula, A., et al., "Structural measurement by inverse scattering in the Rytov approximation", *J. Opt. Soc. Am., 2(11)*, pp. 1958–1960, (Nov. 1985).

Harthog, J., et al., "Thickness measurement for volume holograms by analysis of first–order diffraction", *Applied Optics, 31(11)*, pp. 1803–1809, (Apr. 1992).

Hatab, Z., "Fourier Series Bases Diffraction Tomography Reconstruction of Multidimensional Gratings", Dissertation, University of New Mexico, Albuquerque, New Mexico, pp. 1–123, (May 1998).

Hatab, Z., et al., "Optical Diffraction Tomography for Latent Image Metrology", Poster presentation 1997 SPIE Conference, pp. 1–13, (Mar. 1997).

Hatab, Z.R., et al., "Optical diffraction tomography for latent image metrology", *SPIE, 3050*, pp. 515–524, (1997).

Hatab, Z.R., et al., "Sixteen–megabit dynamic random access memory trench depth characterization using two–dimensional diffraction analysis", *J. Vac. Sci. Technol. B, 13(2)*, pp. 174–182, (1995).

Hickman, K.C., et al., "Use of diffracted light from latent images to improve lithography control", *J. Vac. Sci. Technol. B, 10(5)*, pp. 2259–2266, (1992).

Joachimowicz, N., et al., "Inverse scattering: An iterative numerical method electromagnetic imaging", *IEEE Transactions of Antennas and Propagation, 39(12)*, pp. 1742–1752, (1991).

Kak, A.C., et al., *Principles of Computerized Tomographic Imaging*, IEEE Press, New York, pp. 203–273, (1988).

Kak, A.C., et al., "Computerized Tomography with X–Ray, Emission and Ultrasound Sources", *PRoceedings of the IEEE, 67(9)*, pp. 1245–1272, (Sep. 1979).

Kaveh, M., et al., "Signal Processing for Diffraction Tomography", *IEEE Transactions on Sonics and Ultrasonics, SU–31(4)*, pp. 230–239, (Jul. 1984).

Kirsch, A., "Uniqueness theorems in inverse scattering theory for periodic structures", *Inverse Problems, 10*, pp. 145–152, (1994).

Kleemann, B.H., et al., "Integral equation method with parametrization of grating profile, Theory and experiments", *Journal of Modern Optics, 43(7)*, pp. 1323–1349, (1996).

Koizumi, T., et al., "CD Control using Latent Image for Lithography", *SPIE, 2439*, pp. 418–426, (1995).

Lan, C., et al., "Plane–Scanning Reflection–Diffraction Tomography", *IEEE Transactions on Sonics and Ultrasonics, SU–32(4)*, pp. 562–565, (Jul. 1985).

Lederer, F., et al., "Attenuated thick hologram gratings. Part I: Diffraction efficiency", *Optical and Quantum Electronics, 9*, pp 473–485, (1977).

Lin, F.C., et al., "Image Estimation from Scattered Field Data", *International Journal of Imaging Systems and Technology, 2*, pp. 76–95, (1990).

Ljunghdahl, G., et al., "Surface Scattering near Grazing Angles: The Distorted Wave Born Approximation for Rough Surfaces", *Physics Scripta, 53*, pp. 734–748, (1996).

Mack, C.A., "Absorption and exposure in positive photoresist", *Applied Optics, 27(23)*, pp. 4913–4919, (Dec. 1988).

Marchman, H.M., et al., "Near field optical latent imaging with the photon tunneling microsope", *Appl. Phys. Lett.*, 66(24), pp. 3269–3271, (1995).

Mersereau, R.M., et al., "Digital Reconstruction of Multi-dimensional Signals from Their Projection", *Proceedings of the IEEE*, 62(10), pp. 1319–1338, (Oct. 1974).

Milner, L.M., et al., "Stepper focus characterization using diffraction from latent images", *J. Vac. Sci. Technol. B*, 11(4), pp. 1258–1266, (1993).

Moharam, M.G., et al., "Criteria for bragg regime diffraction by phase gratings", *Optics Communications*, 32(1), pp. 14–18, (Jan. 1980).

Moharam, M.G., et al., "Diffraction analysis of dielectric surface–relief gratings", *J. Opt. Soc. Am.*, 72(10), pp. 1385–1392, (1982).

Moharam, M.G., et al., "Rigorous coupled–wave analysis of grating diffraction — E–mode polarization and losses", *Opt. Soc. Am.*, 73(4), pp. 451–455, (1983).

Moharam, M.G., et al., "Rigorous coupled–wave analysis of metallic surface–relief gratings", *J. Opt. Soc. Am. A*, 3(11), pp. 1780–1787, (Nov. 1986).

Morris, J.B., et al., "Nonlinear filtering applied to single–view backpropagated images of strong scatterers", *J. Opt. Soc. Am.*, 13(7), pp. 1506–1515, (Jul. 1996).

Ocola, L.E., et al., "Scanning force microscopy measurements of latent image topography in chemically amplified resists", *Appl. Phys. Lett.*, 68(5), pp. 717–719, (1996).

Oppenheim, A.V., et al., *Discrete–Time Signal Processing*, Prentice–Hall, New Jersey, pp. 514–580, (1989).

Oppenheim, A.V., et al., *Discrete–Time Signal Processing*, Prentice–Hall, New Jersey, pp. 768–834, (1989).

Otto, G.P., et al., "Microwave inverse scattering——Local shape function imaging for improved resolution of strong scatterers", *IEEE*, pp. 137–141, (1994).

Pan, S.X., et al., "A computational study of reconstruction algorithms for diffraction tomography: Interpolation versus filtered backprogation", *IEEE Transactions on Acoustics, Speech, and Signal Processing*, ASSP–31(5), pp. 1262–1275, (Oct. 1983).

Paul, C.R., et al., "Introduction to Electromagnetic Fields", *McGraw–Hill, New York*, pp. 275–363, (1987).

Petit, R., *Electromagnetic Theory of Gratings*, Springer–Verlag, Barlin, pp. 1–41, (1980).

Rees, C.S., et al., *Theory and Applications of Fourier Analysis*, Marcel Dekker, Inc., New York, pp. 223–245, (1981).

Roger, A., et al., "Inverse scattering method in electromagnetic optics: Application to diffraction gratings", *J. Opt. Soc. Am.*, 70(12), pp. 1483–1495, (1980).

Sammar, A., et al., "Diffraction of multilayer gratings and zone plates in the X–ray region using the Born approximation", *J. Opt. Soc. Am. A*, 10(4), pp. 600–613, (Apr. 1993).

Shanmugan, K.S., et al., *Random Signals: Detection, Estimation, and Data Analysis*, John Wiley & Sons, New York, pg. 330, (1988).

Slaney, M., et al., "Limitations of Imaging with First–Order Diffraction Tomography", *IEEE*, pp. 860–874, (Aug. 1984).

Sohail, S., et al., "Analysis of a strip–grating twist reflector", *J. Opt. Soc. Am. A*, 7(9), pp. 1723–1729, (Sep. 1990).

Sohail, S., et al., "Diffractive techniques for lithographic process monitoring and concert", *J. Vac. Sci. Technol. B*, 12(6), pp. 3600–3606, (1994).

Stark, H., *Image Recovery: Theory and Application*, Academic Press, Inc., Orlando, pp. 369–413, (1987).

Steiglitz, K., et al., "Phase unwrapping by factorization", *IEEE Transactions on Accoustics, Speech, and Signal Processing*, ASSP–30(6), pp. 984–991, (Dec. 1982).

Sturtevant, J.L., et al., "Post–exposure bake as a process–control parameter for chemically–amplifide photoresist", *SPIE*, 1926, pp. 106–114, (1993).

Tenner, M.G., "A scanning optical microscope integrated in a wafer stepper for image sensing", *SPIE*, 2725, pp. 652–658, (1996).

Tribolet, J.M., "A New Phase Unwrapping Algorithm", *IEEE Trasnactions on Acoustics, Speech, and Signal Processing*, ASSP–25(2), pp. 170–177, (1977).

Wedberg, T.C., et al., "Experimental examination of the quantitative imaging properties of optical diffraction tomography", *J. Opt. Soc. Am.*, 12(3), pp. 493–500, (Mar. 1995).

Wolf, E., "Determination of the Amplitude and the Phase of Scattered Fields by Holography", *Journal of the Optical Society of America*, 60(1), pp. 18–20, (1970).

Wolf, E., "Three–dimensional structure dtermination of semi–transparent objects from holographic data", *Optics Communications*, 1(4), pp. 153–156, (Sep. 1969).

Yoon, E., et al., "Latent image diffraction from submicron photoresist gratings", *J. Vac. Sci. Technol. B*, 10(5), pp. 2230–2233, (1992).

Yoon, E., et al., "Phase–contrast latent image metrology for microlithography", *SPIE, 1673, Integrated Circuit Metrology, Inspection, and Process Control VI*, pp. 580–591, (1992).

Ziemer, R.E., et al., *Signals and Systems: Continuous and Discrete*, Macmillan Publishing Company, New York, pp. 83–130, (1989).

* cited by examiner

DIFFRACTION TOMOGRAPHY FOR MONITORING LATENT IMAGE FORMATION This is a non-provisional patent application claiming priority to provisional patent application Serial No. 60/047,530, filed on May 23, 1997, entitled: DIFFRACTION TOMOGRAPHY FOR LATENT IMAGE METROLOGY, by Ziad R. Hatab.

BACKGROUND OF THE INVENTION

1. Field of the Invention

The present invention is related to integrated circuit manufacturing, and more particularly to the use of diffraction tomography for latent image metrology.

2. Background Information

Integrated circuits are manufactured through a sequence of controlled steps used to form layers of conducting, insulating and transistor-forming materials. Layers within the integrated circuit are formed by covering the surface of a wafer with photoresist and exposing selected portions of the photoresist to light at a particular wavelength.

The exposure process begins when an exposing light source, traveling through a photomask containing the desired patterns, falls incident on the wafer. The photoresist is exposed to the light source traveling through the photomask, and depending on the photomask's geometry, the photoresist consequently undergoes gradual refractive index changes between the exposed region and the unexposed region. The changes in the photoresist due to exposure may not be visible at this point. That is why the image is termed a latent image. The photoresist is then developed and the unexposed areas are washed away.

Latent image formation is a critical time in the manufacturing process. If the photoresist has been underexposed, the features formed in the developed photoresist may be too small to perform correctly. To date, the methods used to monitor latent image formation have been limited to either microscope inspection or diffraction measurement.

Microscope inspection cannot be done real time. Microscope inspection typically requires a complicated setup. Furthermore, the wafer usually must be taken from the fab line to the microscope to be inspected.

Diffraction measurement techniques used to date have been limited to heuristic approaches which correlate the intensity of diffractions to final critical dimension (CD) measurements. For instance, one would measure intensities of the first diffraction order and, after development of the photoresist, measure the resulting critical dimension. Such an approach is very inflexible. That is, any change to manufacturing parameters such as exposure intensity or duration, or in the chemistry of the photoresist, forces the manufacturer to go through the entire correlation process all over again.

What is needed is a system and method for monitoring latent image formation which can be done in close to real time, yet which is flexible enough to accommodate changes in the manufacturing process.

SUMMARY OF THE INVENTION

The present invention is a system and method of reconstructing an image of a structure having periodic variations in index of refraction. Electromagnetic waves are projected onto the structure and the resulting diffracted electromagnetic waves are measured, wherein the step of measuring includes the step of determining a plurality of intensities DE. Refractive terms can then be calculated as a function of the intensities DE.

According to one aspect of the present invention latent image formation in photoresist can be measured by forming a periodic structure such as a grating in the photoresist. Light is projected onto the structure and the resulting diffracted light is measured, wherein the step of measuring includes the step of determining a plurality of intensities DE. Refractive terms can then be calculated as a function of the intensities DE.

According to another aspect of the present invention, a stepper can be constructed which can monitor latent image formation in photoresist. The stepper includes a fixture for receiving a wafer and a photomask, a first light source for illuminating the wafer through the photomask and at a first incident angle, a second light source positioned to illuminate the wafer at a second incident angle, wherein the second angle is different from the first incident angle and a detector positioned to measure light diffracted from the wafer.

According to yet another aspect of the present invention, a track can be constructed which can monitor latent image formation in photoresist. The track includes a bake chamber, a development chamber, a light source positioned to illuminate the wafer at an incident angle and a detector positioned to measure light diffracted from the wafer.

BRIEF DESCRIPTION OF THE DRAWINGS

FIGS. 9 and 10 illustrate n(x, z) for N=1 and N=2 respectively, with selected values of $n_0$, $n_1$, $n_2$; and FIG. 11 is a flow chart of the reconstruction of a latent image.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
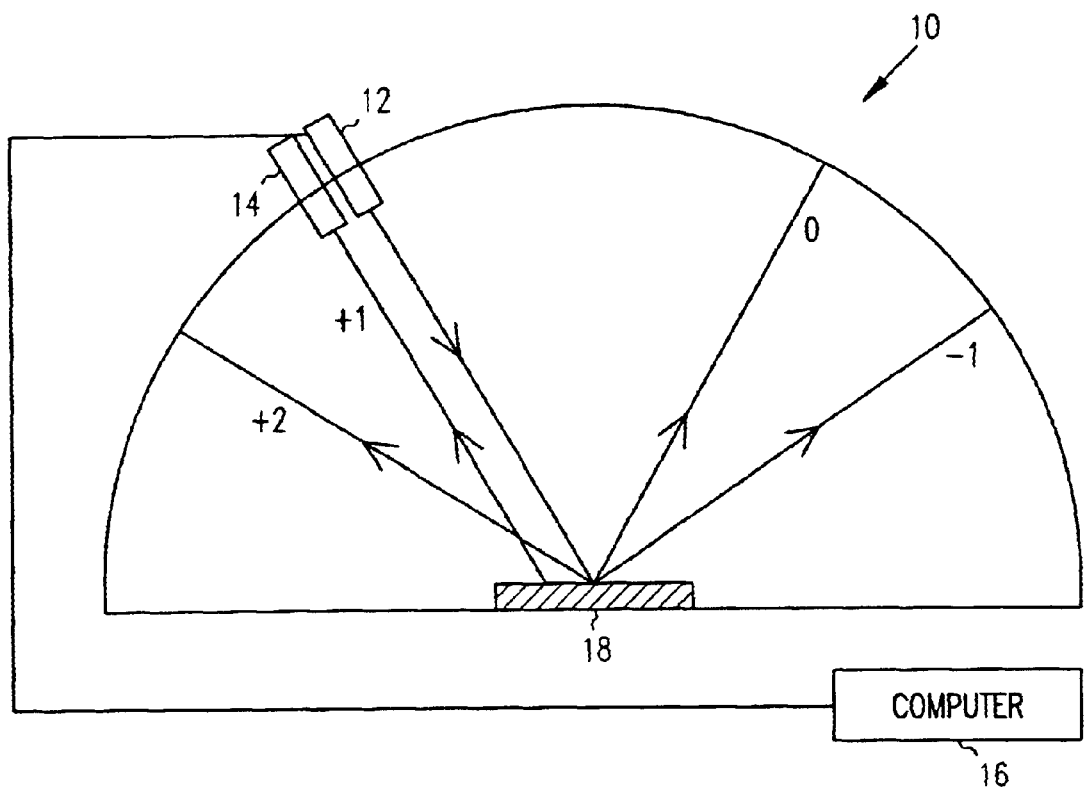
FIG. 1 is a latent image measurement system according to the present invention.

FIG. 1 illustrates a system for measuring latent image formation in a periodic structure such as a diffraction grating. System 10 includes a light source 12 and a detector 14 connected to a computer 16. Light source 12 is used to illuminate wafer 18 in order to reconstruct the latent image formed inside the layer of photoresist coating wafer 18. In one embodiment, computer 16 controls light source 12 and uses the reflected light measured at detector 14 to reconstruct the pattern imaged onto the photoresist.

In order to measure latent image formation according to the present invention, one must form a periodic structure as part of the latent image. The periodic structure could be a special diffraction grating formed in a section of the wafer, or it could be an approximately periodic structure identified within the device being manufactured on wafer 18.

As noted above, in one embodiment the exposure process begins when an exposing light source, traveling through a photomask containing the desired patterns, is incident on wafer 18. The photoresist is exposed to the light source traveling through the photomask, and depending on the photomask's geometry, the photoresist consequently undergoes gradual refractive index changes between the exposed region index, $n_2$ and the unexposed region index, $n_1$. These changes vary rather slowly, almost in sinusoidal fashion, with magnitudes comparable to the background's refractive index, i.e., air (n=1). These variations are in agreement with the weakly scattering conditions of the Born approximation. Next, the photoresist is developed and the unexposed areas are washed away. The end result is a periodic train of pulses with refractive index n, period D, and width commonly referred to as critical dimension (CD).

As noted above, it would be advantageous to be able to determine the results of the exposure of the photoresist before the photoresist is developed (i.e., at the latent image stage). This is possible using diffraction tomography.

Diffraction tomography (DT) falls under the general area of inverse scattering. The purpose of inverse scattering is to reconstruct multidimensional objects from the subset of lower dimensional information or projections. This is accomplished by illuminating the objects at certain electromagnetic wavelengths from different directions and collecting the diffracted data or projections for inversion. Projections are defined generally as the mapping of an N-dimensional object to an (N−1)-dimensional function by integrating the object on a particular path.

The projection integration path mentioned above is application dependent. For example, in X-Ray tomography when the incident wavelength is much smaller than the size of the object (λ<<D), electromagnetic waves obey classical ray theory and propagate along straight lines through the object. For this case, the integration path is along straight lines and object reconstruction is accomplished via the well-known backprojection algorithm. On the other hand, when using acoustic or optical sources the incident wavelength becomes comparable in dimension to the size of the object and the waves no longer travel in straight lines but experience diffraction. In this case, as will be shown later, the integration path is semicircular. Different imaging algorithms for the diffracting case have been developed which fall under the following two categories: spatial domain algorithms, such as the backpropagation algorithm, and frequency domain algorithms, such as the Unified Fourier Reconstruction (UFR) algorithm.

Diffraction tomography has been successfully applied to different areas such as medical imaging, geophysical sensing, and industrial inspection. Moreover, diffraction tomography can employ the reflected field, or the transmitted field, or both fields in its reconstructions depending on the application. When optical wavelengths are used, the technique is referred to as optical diffraction tomography (ODT). The most common application of ODT rests in the area of nondestructive evaluation. The goal is to reconstruct the refractive index profile of an object without affecting its optical properties. The incident field is usually a laser operating at nonexposing wavelengths.

The system shown in FIG. 1 reconstructs periodic objects, known also as gratings, using reflected diffraction data. Previous and current work in ODT concentrated solely on reconstructing single aperiodic objects using transmitted diffraction data. Unfortunately, in the case of latent image metrology, the transmitted field is not readily available. In addition, when interrogating aperiodic objects, the diffracted field is continuous. On the other hand, the periodic nature of the gratings used to study latent image formation restricts the diffracted field to reside in a discrete and finite number of propagating orders (orders 0, 1,−1, etc.), thus limiting the number of available data points.

The refractive index distribution of latent images can be reconstructed and the results used to control developed CD patterns. This technique requires as input the diffracted field, complex or magnitude, from latent images generated by a nonexposing source incident at different viewing angles. The ODT algorithm in turn produces at the output the reconstructed latent image.

Figure 2:
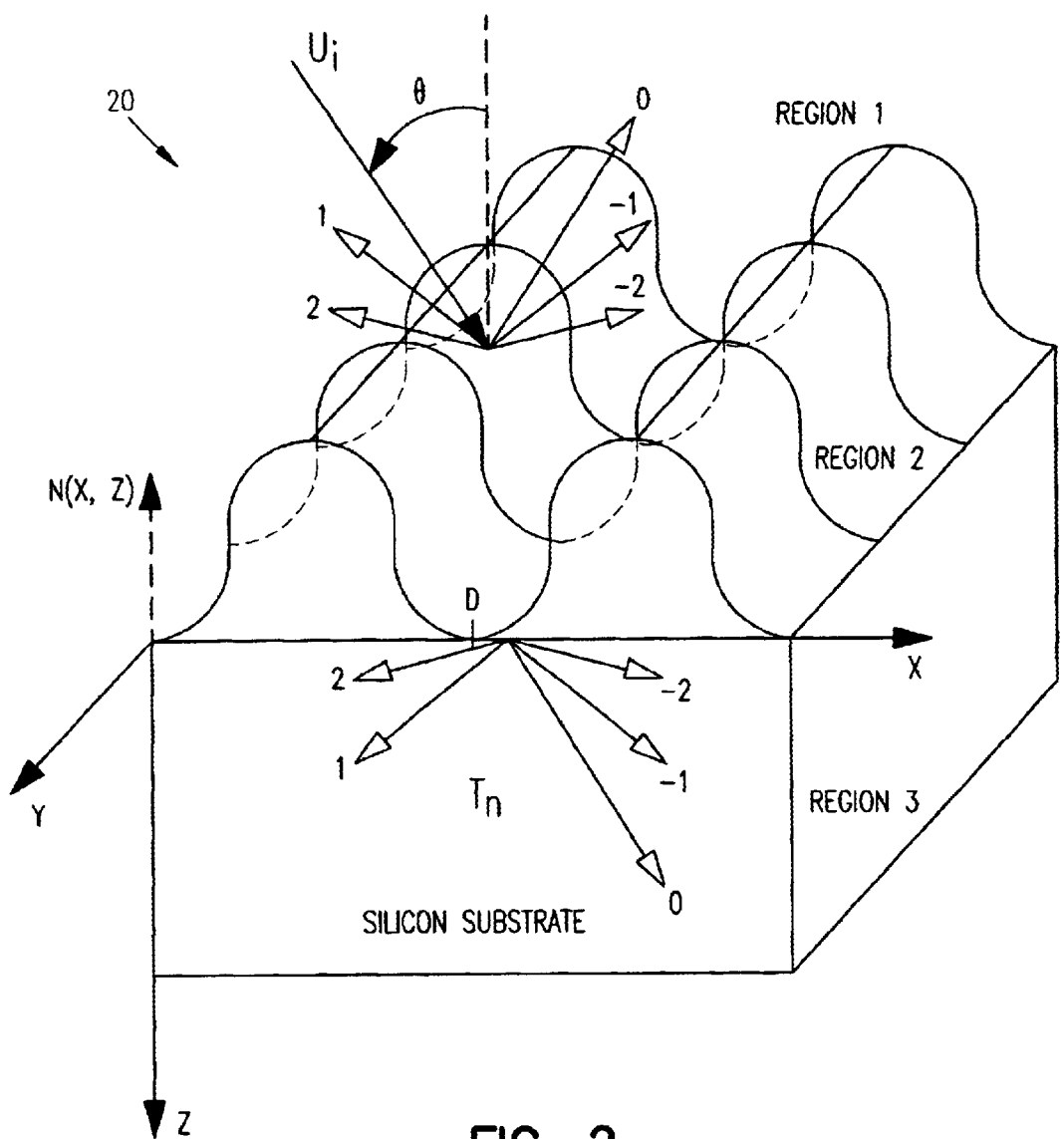
FIG. 2 is an illustration of a two-dimensional latent image grating.

The geometry of a two-dimensional latent image grating 20 treated is shown in FIG. 2 An electromagnetic wave, $E_i$, obliquely incident upon the grating, produces both forward diffracted (transmitted) and backward diffracted (reflected) waves. Region 1 is the input region with relative permittivity $\epsilon_1$. Region 1 is usually air (i.e., $\epsilon_1$=1). Region 2 contains the grating denoted by its two-dimensional periodic complex refractive index distribution n(x, z), period D, and height W. Region 3 contains a substrate (e.g., silicon) having relative permittivity $\epsilon_3$. In a typical situation, the transmitted waves are absorbed as they propagate in region 3 through the substrate, hence limiting this technique to reflected waves only. In cases where the transmitted waves are available and detectable, they may be used in the reconstruction process. The transmitted waves, if available, can be used to improve the quality of the image reconstruction.

In the following, we assume the case when the incident wave lies parallel to the grating (transverse electric polarization or TE). The total electric field, $u_1$, in region 1 is the sum of the incident field, $u_i$, and backward diffracted field, $u_{d1}$, $$u_1(x,y,z) = u_i(x,y,z) + u_{d1}(x,y,z), \quad (1)$$

or in expanded form $$u_1(x, y, z) = e^{-j(k_{x0}x + k_{z0}z)} + \sum_{n=-\infty}^{\infty} R_n e^{-j(k_{xn}x - k_{zn}z)} \quad (2.1)$$

where $k_{x0} = k_1 \epsilon_1^{1/2} \sin\theta$, $k_{z0} = k_1 \epsilon_1^{1/2} \cos\theta$, $k_1 = 2\pi/\lambda$ is the wave number, θ is the angle of incidence, λ is the free-space wavelength, and $R_n$ is the complex reflection coefficient of the nth-order backward diffracted wave. Similarly, the Rayleigh expansion of the electromagnetic field, $u_3$, in region 3 is given by the forward diffracted field, $u_{d3}$, $$u_3(x, y, z) = u_{d3}(x, y, z) = \sum_{N=-\infty}^{\infty} T_n e^{-j[k_{xn}x + k_{zn3}(z-W)]} \quad (2.2)$$

where $T_n$ is the complex transmission coefficient of the nth-order forward diffracted wave. Given n(x, z), the $R_n$s and $T_n$s are calculated using different electromagnetic modeling techniques. This is known as the forward scattering problem.

We will use rigorous coupled wave analysis (RCWA) to determine the complex reflection coefficients and the diffraction efficiencies of a certain grating profile. On the other hand, the inverse scattering problem consists of determining n(x, z) from the $R_n$s. Going back to equations (2.1 and 2.2), we further have $$k_{xn} = k_{x0} - nK = k_1 \epsilon_1^{1/2} \sin\theta - n2\frac{\pi}{D}, \quad (3)$$

where n=0, ±1, ±2, ±3, . . . is the nth-diffracted order and K is the magnitude of the grating vector. The case n=0 corresponds to specular reflection. In addition $$k_{zn} = \begin{cases} \sqrt{k_1^2 \epsilon_1 - k_{xn}^2}; & |k_{xn}| \leq k_1 \sqrt{\epsilon_1} \\ j\sqrt{k_{xn}^2 - k_1^2 \epsilon_1}; & |k_{xn}| > k_1 \sqrt{\epsilon_1} \end{cases} \quad (4)$$

$k_{xn}$ and $k_{zn}$ are the wave vectors in the x and z directions, respectively of the nth-diffracted order, and $j=\sqrt{-1}$. The real form of $k_{zn}$ corresponds to propagating waves, while the imaginary form corresponds to evanescent waves, i.e., damped waves traveling along the x axis. We are mainly interested in propagating waves. Finally, we have $$k_{zn3} = \sqrt{k_1^2 \epsilon_3 - k_{xn}^2} \quad (4)$$

It can be shown that the diffracted field satisfies the following wave equation $$\nabla^2 E_d(\vec{r}) + k_1^2 E_d(\vec{r}) = o(x,z)E(\vec{r}) \quad (5)$$

where $\nabla^2$ is the Laplacian operator, $\vec{r} = (x,y,z)$ and $$o(x,z) = k_1^2 [1 - n^2(x,z)] \quad (6)$$

is the scattering potential or object function. The goal is to determine o(x, z) from the diffracted field, $E_d$, for according to equation (6), knowledge of o(x, z) is equivalent to the knowledge of n(x, z).

Since o(x, z) is periodic in the x direction with period D, or o(x, z)=o(x+D, z), it is necessary to consider a truncated portion of it, namely $o_\tau(x, z,)$, over one period.

$$o_\tau(x, z) = \begin{cases} o(x, z) & 0 \leq x \leq D \\ 0; & \text{otherwise} \end{cases} \quad (7)$$

The solution to equation (5) is usually written in integral form as a function of the Green's function, g(x, z), $$E_d(\vec{r}) = \int g(\vec{r} - \vec{r}') o(\vec{r}') E(\vec{r}') d\vec{r}' \quad (8)$$

Equation (8) is a Fredholm integral equation of the second kind and is a solution to the diffracted field $E_d$ in both regions 1 and 3.

It is not generally possible or desirable to directly solve for equation (8). Its solution may be computationally difficult for arbitrary o(x, z). One way of simplifying it is to linearize equation (8) through the use of linearizing approximations such as the weakly scattering or first Born approximation. The first Born approximation assumes that the diffracted field is much smaller than the incident field, and that, therefore, $$E(\vec{r}) = E_0(\vec{r}) = E_i(\vec{r}). \quad (9)$$

This approximation is in accordance with the weakly scattering nature of the latent image gratings discussed earlier.

Substituting equation (9) into (8) we obtain the following simplified Fredholm integral equation $$E_d(\vec{r}) = \int g(\vec{r} - \vec{r}') o(\vec{r}') E_i(\vec{r}') d\vec{r}', \quad (10)$$

$$E_d(\vec{r}) = \int_{-\infty}^{\infty} \int_0^D \int_0^W g(\vec{r} - \vec{r}') o(\vec{r}') E_i(\vec{r}') dz' dx' dy', \quad (11)$$

At this point, the above integral is in its general three-dimensional form. However, since the grating is invariant along the y-direction, the dependence on y in equation (11) is ignored and the problem is reduced to a two-dimensional one, $$E_d(\vec{r}) = \int_0^D \int_0^W g(\vec{r} - \vec{r}') o(\vec{r}') E_i(\vec{r}') dz' dx'. \quad (12)$$

The first Rytov approximation can be used in a similar fashion to achieve a solution to the diffracted field $E_d$.

Substituting expressions for the incident field and Green's function into equation (11) and performing the calculations, we obtain the following important relationship for the case of reflection tomography $$R_n = \frac{1}{j4\pi D k_{zn}} O_\tau(K_x, K_z). \quad (13)$$

where $O_\tau(K_x, K_z)$ is the two-dimensional Fourier transform of $o_\tau(x, z)$ in the $(K_x, K_z)$ frequency plane and where $$K_x = -k_{xn} + k_{x0} = n2\pi/D, \text{ and } K_z = k_{zn} + k_{z0} = \sqrt{k_1^2 - k_{xn}^2} + k_1 \cos\theta.$$

Equation (13) relates the two-dimensional Fourier transform of the object function to the one-dimensional complex reflection coefficients. It is also commonly referred to as the Fourier diffraction theorem. Therefore, from the complex reflection coefficients $R_n$s of the Born approximation, the Fourier transform of the object is reconstructed as follows $$O_\tau(K_x, K_z) = j4\pi D k_{zn} R_n. \quad (14.1)$$

Likewise, from the Rytov complex reflection coefficients $D_n$s, the Fourier transform of the object is reconstructed as follows $$O_\tau(k_x, k_z) = j4\pi D k_{zn} D_n \quad (14.2)$$

However, even though the complex reflection coefficient are computed numerically via a rigorous electromagnetic solver program (e.g., a rigorous coupled wave analysis (RCWA) computer program), experimentally one usually only measures the intensities of $R_n$s or diffraction efficiencies (DE) defined as $$DE_{1n} = |R_n|^2 \frac{k_{zn}}{k_{z0}}, \quad (15.1)$$

for the Born approximation and as $$DE_{1n} = |D_n|^2 \frac{k_{zn}}{k_{z0}}, \quad (15.2)$$

for the Rytov approximation, where $DE_{1n}$ is the diffraction efficiency of the nth-order reflected wave in region 1. Hence, equations (14.1 and 14.2) are rewritten in magnitude form as $$|O_\tau K_x, K_z)|^2 = |j4\pi D k_{zn}|^2 DE_n \frac{k_{z0}}{k_{zn}}. \quad (16)$$

Two types of reconstructions are now possible. In equations (14.1 and 14.2) the phase information is incorporated into the reconstruction process through the complex reflection coefficients, while equation (16) operates only on intensity data with no phase content.

It is therefore possible to reconstruct the Fourier estimate of the object function using two types of tomography: reflection tomography and transmission tomography. For reflection tomography $$|F\{o_\tau(x, z)\}|^2 = |O_\tau(K_x, K_z)|^2 = |j4\pi D k_{zn}|^2 DE_{1n} \frac{k_{z0}}{k_{zn}} \quad (17)$$

where F{ } denotes the Fourier operator $$K_x = -k_{xn} + k_{x0} = nK = n^{2\pi}/_D \quad (18)$$

$$K_z = k_{zn} + k_{z0} = \sqrt{k_1^2 \epsilon_1 - k_{xn}^2} + k_1 \epsilon_1^{1/2} \cos\theta \quad (19)$$

and, $$K'_z = -k_{zn3} + k_{z0} = -\sqrt{k_1^2 \epsilon_3 - k_{xn}^2} + k_1 \epsilon_1^{1/2} \cos\theta \quad (20)$$

while for transmission tomography $$|F\{o_\tau(x, z)\}|^2 = |O_\tau(K_x, K_z)|^2 = |j4\pi D k_{zn3} e^{jk_{zn3}W}|^2 DE_{3n} \frac{k_{z0}}{k_{zn3}} \quad (21)$$

The diffraction efficiencies are estimated using either the first Born or Rytov approximations.

At first it may appear that the problem of reconstructing o(x, z) is straightforward hereafter; sample O(K$_x$,K$_z$) at different viewing angles and then inverse Fourier transform the result according to Equations (14.1 and 14.2). But it is not that simple. The fact that the frequency domain samples are available over circular arcs is a source of computational difficulty in reconstruction algorithms for diffraction tomography. For proper Fourier inversion, it is desirable to have samples over a rectangular or Cartesian grid. Another important restriction in ODT lies in the limited number of viewing angles. As illustrated in FIG. 1, the range of incident angles is confined to 180 degrees range, i.e., from −90 to 90 degrees. Beyond these limits, the electric field is no longer incident on the grating. The effect is to leave holes where there are no estimates of the Fourier transform of the object and consequently to degrade the reconstruction. Different frequency and spatial domain algorithms for interpolating the semicircular frequency data into rectangular frequency data, and for interpolating the missing data have been proposed and implemented by Devaney and by Kaveh et al. However, it is important to keep in mind that these algorithms were specifically developed for single aperiodic objects and their extension to periodic objects proved ineffective. Hence, a new reconstruction algorithm tailored to our specific need was necessary.

Equations 14.1 and 14.2 are further simplified by considering that the index of refraction inside the photoresist can be expressed as $$n(x, z) = n_0 + \sum_{i=1}^{\infty} n_i \cos\left(2\pi \frac{xi}{D}\right). \quad (22)$$

The problem is now reduced to determining $n_0$ and $n_i s_i$ for the case where i=1 (i.e., the sinusoidal case). Substituting Equation (22) into Equation (6), we obtain $$o(x, z) = k_1^2 \left[1 - n_0^2 - \frac{1}{2}n_1^2 - 2n_0 n_1 \cos\left(2\pi\frac{x}{D}\right) - \frac{n_1^2}{2}\cos\left(4\pi\frac{x}{D}\right)\right]. \quad (23)$$

Similar expansions can be calculated for higher i terms. We are now able to evaluate the Fourier transform of $o_\tau(x, z)$, namely $O_\tau(K_x, K_z)$, given by $$O_\tau(K_x, K_z) = \int_{-D/2}^{D/2} \int_{-W/2}^{W/2} o_\tau(x, z) e^{-jK_x x} e^{-jK_z z} dx dz. \quad (24)$$

Carrying out the calculations and keeping in mind that o(x, z) can be expanded in a Fourier series as $$o(x, z) = \sum_{m=-\infty}^{\infty} O_m e^{\frac{jm2\pi x}{D}}, \quad (25)$$

where $O_m$ is the mth-exponential Fourier series coefficient, we obtain the following result $$O_\tau(K_x, K_z) = DW \operatorname{sinc}\left(K_z \frac{W}{2\pi}\right) \sum_{m=-2N}^{2N} O_m \operatorname{sinc}(n - m). \quad (26)$$

where sinc [ ] is the sinc function defined as $$\operatorname{sinc}[x] = \frac{\sin \pi x}{\pi x} \quad (27)$$

The −2N to 2N summation limits in Equation (26) are due to the presence of the $n^2$ (x,z) term in calculating o(x,z); for every N sinusoidal terms in n(x,z) we have 2N sinusoidal terms in o(x,z) as illustrated in Equation (3.6) for the case i=1. Equating both equations (26) and (16) yields the following relationship $$|O_n|^2 = \frac{16\pi^2 k_{zn} k_{z0}}{W^2 \operatorname{sinc}^2\left(K_z \frac{W}{2\pi}\right)} DE_{1n} \quad (28)$$

Equation (28) can be used to solve both forward and inverse scattering problems in complex or magnitude form. In the following discussion, equation (28) will be referred to as the Fourier Series Reconstruction (FSR) techniques. However, we are only interested in the inverse problem, and diffraction efficiencies are more readily available than complex reflection coefficients. It is apparent from Equation (23) that, for the sinusoidal case (i.e., i=1)

$$O_2 = \frac{n_1^2}{4} k_1^2 \text{ and } O_1 = -n_0 n_1 k_1^2.$$

Hence by measuring the +2 and +1 diffracted orders at their respective Bragg angles (see FIGS. 1 and 11) and solving Equation (28), we can determine $n_0$ and $n_1$. The Bragg angle for the nth diffracted order is obtained from the grating formula $$\sin\theta_n = \sin\theta + n\frac{\lambda}{D}. \quad (29)$$

by setting $\theta_n = -\theta$.

The following numerical results were obtained from simulated data. The diffraction efficiencies for a given latent image distribution, $n(x, z)$, were calculated using an RCWA computer program. Given the +2 and +1 diffraction efficiencies at their respective Bragg angles, Equation (28) was solved for different latent image gratings as illustrated in Table 1. The incident wavelength was chosen in the visible red range, $\lambda = 0.6328$ μm.

It is apparent from Table 1 that the ODT reconstructed $n_1$ values more closely matched their simulated counterparts than the reconstructed $n_0$ values. The $n_0$ values had a larger error because of their dependence on $n_1$ in the calculations; any errors introduced in the calculation of $n_1$ were carried onto the calculation of $n_0$ as observed from the first Fourier exponential series coefficient of $o(x, z)$, $O_1$. In addition, as the grating was made thicker the results became less accurate, leading us to the conclusion that the Born approximation is heavily dependent on the grating thickness; gratings need to be "thin" for the Born approximation to hold and for this technique to be applicable. Unfortunately, it is not possible to establish theoretical bounds for the Born regime, and consequently, defining "thin" gratings becomes application dependent. For our specific simulation parameters, a grating thickness of less than 30 nm satisfied the Born conditions. By changing different parameters (e.g., incident wavelength, period), this limit is bound to move. Moreover, variations in period D hardly altered the results. However, the period should be such that the presence of the (+2) and (+1) diffraction orders at their Bragg angles is guaranteed. FIGS. 9 and 10 illustrate $n(x, z)$ for N=1 and N=2 respectively, with selected values of $n_0$, $n_1$, $n_2$.

TABLE 1

ODT reconstruction results

| Grating parameters | Height, W (μm) | Period, D (μm) | Reconstructed $n_0$ | Reconstructed $n_1$ |
|---|---|---|---|---|
| $n_0 = 1.1$, $n_1 = 0.01$ | 0.01 | 1.5 | 1.185 | 0.0097 |
| $n_0 = 1.2$, $n_1 = 0.02$ | 0.01 | 1.5 | 1.291 | 0.0194 |
| $n_0 = 1.3$, $n_1 = 0.03$ | 0.01 | 1.5 | 1.397 | 0.0292 |
| $n_0 = 1.4$, $n_1 = 0.04$ | 0.01 | 1.5 | 1.503 | 0.0390 |
| $n_0 = 1.5$, $n_1 = 0.05$ | 0.01 | 1.5 | 1.607 | 0.0489 |
| $n_0 = 1.6$, $n_1 = 0.06$ | 0.01 | 1.5 | 1.711 | 0.0588 |
| $n_0 = 1.6$, $n_1 = 0.06$ | 0.03 | 1.5 | 1.746 | 0.0726 |
| $n_0 = 1.6$, $n_1 = 0.06$ | 0.05 | 1.5 | 1.870 | 0.1038 |
| $n_0 = 1.6$, $n_1 = 0.06$ | 0.01 | 2.5 | 1.679 | 0.0610 |

By following the procedures outlined above, similar relationships can be obtained for expansions with higher N values. In Table 2 below, we give expressions for the $O_m$s up to N=4. These values, in conjunction with Equation (27) are crucial in reconstructing $n_0$ and $n_i$s. From the results presented in Table 2 below, we notice the following patterns in reconstructing the $n_i$s. First, for an Nth-order series expansion of $n(x,z)$, it is imperative to be able to measure 2N diffraction orders. Next, excluding $n_0$, the highest modulation refractive term, $n_N$, is always determined first from a measurement of the 2N th diffraction efficiency, $DE_{1(2N)}$. Next, in conjunction with $n_N$, the second highest modulation refractive term, $n_{N-1}$, is determined from a measurement of the (2N−1)th diffraction efficiency, $DE_{1(2N-1)}$. The process is thus continued until we reach the first modulation term, $n_1$, which is determined from a measurement of the (N+1)th diffraction efficiency, $DE_{1(N-1)}$, and estimates of the $n_2$, $n_3$, ... $n_{N-1}$, $n_N$ refractive indices. Thus, for an Nth-order series expansion of $n(x,z)$, we need to measure the 2N, 2N−1, ..., N+2, N+1 diffraction orders to fully reconstruct the refractive index modulation factors. Diffraction orders below the N+1th diffraction order, i.e., N, N−1, ..., 2, 1, contain redundant and ambiguous information on estimating the average refractive index, $n_0$. Consequently, estimating $n_0$ from these diffraction orders should be performed with extreme caution; for an Nth order series expansion of $n(x,z)$, there are N different ways of estimating $n_0$.

TABLE 2

| | N = 1 | N = 2 | N = 3 | N = 4 |
|---|---|---|---|---|
| $O_1$ | $-k_1^2 n_0 n_1$ | $-k_1^2\left(n_0 n_1 + \frac{n_1 n_2}{2}\right)$ | $-k_1^2\left(n_0 n_1 + \frac{n_1 n_2}{2} + \frac{n_2 n_3}{2}\right)$ | $-k_1^2\left(n_0 n_1 + \frac{n_1 n_2}{2} + \frac{n_2 n_3}{2} + \frac{n_3 n_4}{2}\right)$ |
| $O_2$ | | $-k_1^2 \frac{n_1^2}{4}$ | $-k_1^2\left(\frac{n_1^2}{4} + n_0 n_2\right)$ | $-k_1^2\left(\frac{n_1^2}{4} + n_0 n_2 + \frac{n_1 n_3}{2}\right)$ | $-k_1^2\left(\frac{n_1^2}{4} + n_0 n_2 + \frac{n_1 n_3}{2} + \frac{n_2 n_4}{2}\right)$ |
| $O_3$ | | | $-k_1^2 \frac{n_1 n_2}{2}$ | $-k_1^2\left(\frac{n_1 n_2}{2} + n_0 n_3\right)$ | $-k_1^2\left(\frac{n_1 n_2}{2} + n_0 n_3 + \frac{n_1 n_4}{2}\right)$ |
| $O_4$ | | | | $-k_1^2 \frac{n_2^2}{4}$ | $-k_1^2\left(\frac{n_2^2}{4} + \frac{n_1 n_3}{2}\right)$ | $-k_1^2\left(\frac{n_2^2}{4} + \frac{n_1 n_3}{2} + n_0 n_4\right)$ |

TABLE 2-continued

| | N = 1 | N = 2 | N = 3 | N = 4 |
|---|---|---|---|---|
| $O_5$ | | | $-k_1^2 \dfrac{n_2 n_3}{2}$ | $-k_1^2\left(\dfrac{n_2 n_3}{2} + \dfrac{n_1 n_4}{2}\right)$ |
| $O_6$ | | | $-k_1^2 \dfrac{n_3^2}{4}$ | $-k_1^2\left(\dfrac{n_3^2}{4} + \dfrac{n_2 n_4}{2}\right)$ |
| $O_7$ | | | | $-k_1^2 \dfrac{n_3 n_4}{2}$ |
| $O_8$ | | | | $-k_1^2 \dfrac{n_4^2}{4}$ |

The practicality of this solution for higher N values becomes questionable especially since an expansion of order N requires 2N diffracted orders. For example, an n(x,z) expansion with N=4 requires the successful measurement of 4 weakly scattering diffraction orders, namely orders 8, 7, 6; and 5, to determine $n_4$, $n_3$, $n_2$, and $n_1$ respectively. In addition, the number of diffraction orders is dependent on the wavelength, λ and period, D. For a given wavelength, λ, the grating's period, D, may have to be substantially increased to obtain 8 diffracted orders. Alternatively, for a given period, D, the wavelength, λ, may have to be substantially decreased to obtain 8 diffracted orders. Such limitations may render this technique unsuitable for refractive index profiles with sharp transitions. However, as will be shown later, perfect reconstructions were obtained for slowly varying index profiles such as the ones encountered in latent image gratings.

To summarize, this technique appears to be well-suited for reconstructing the refractive index modulation values, $n_i$s, in a slowly varying medium. For a medium with sharp transitions, this technique is applicable so long as the combination of period D and wavelength λ is such that all the required diffraction orders are available. In addition, the average refractive index value, $n_0$, may be reconstructed using this technique; however, extreme caution must be employed when doing so, especially when the number of possible solutions becomes rather large (more than 2 solutions).

The ODT reconstruction algorithm presented here is based on the formulation of the wave equation and its solution under the Born approximation. Hence, this technique offers a general solution to the inverse scattering problem in latent image metrology and consequently, in developed resist metrology.

Figure 3A:
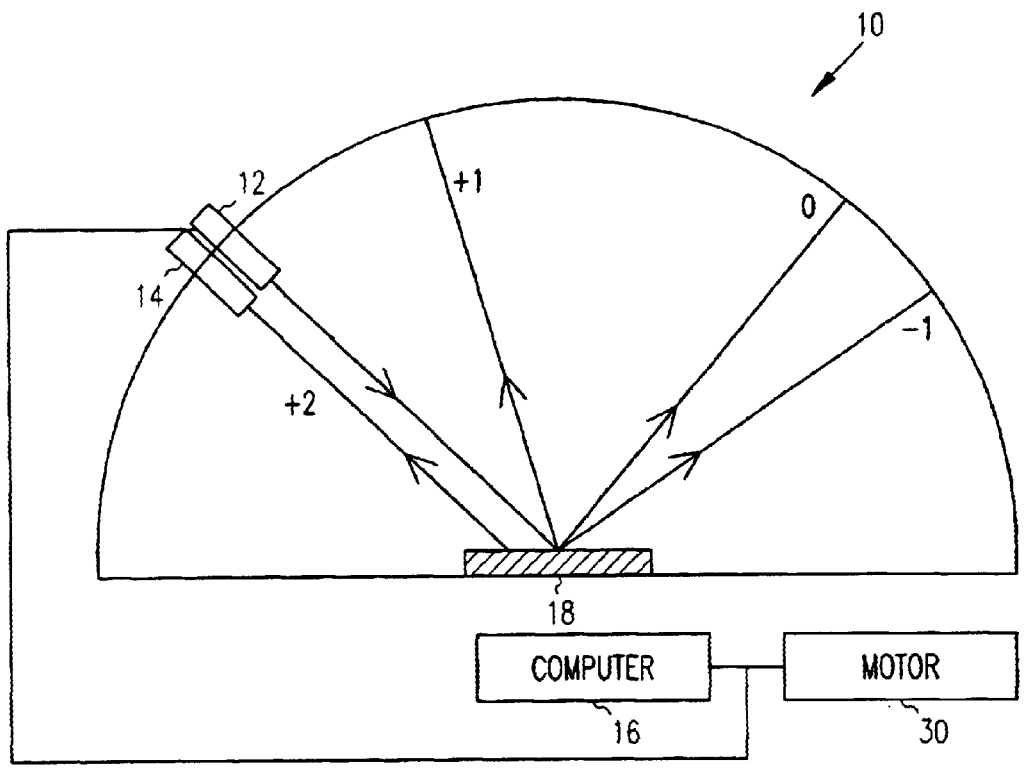
FIGS. 3a–3c are alternate embodiments of the latent image measurement system of FIG. 1.

FIG. 3a illustrates another embodiment of a latent image measurement system 10 according to the present invention. In the embodiment shown in FIG. 3a, light source 12 and detector 14 are mounted on a rail and can be moved to the desired Bragg angle under control of motor 30. In one such embodiment, computer 16 controls motor 30 in order to position detector 14 and light source 12.

Figure 3B:
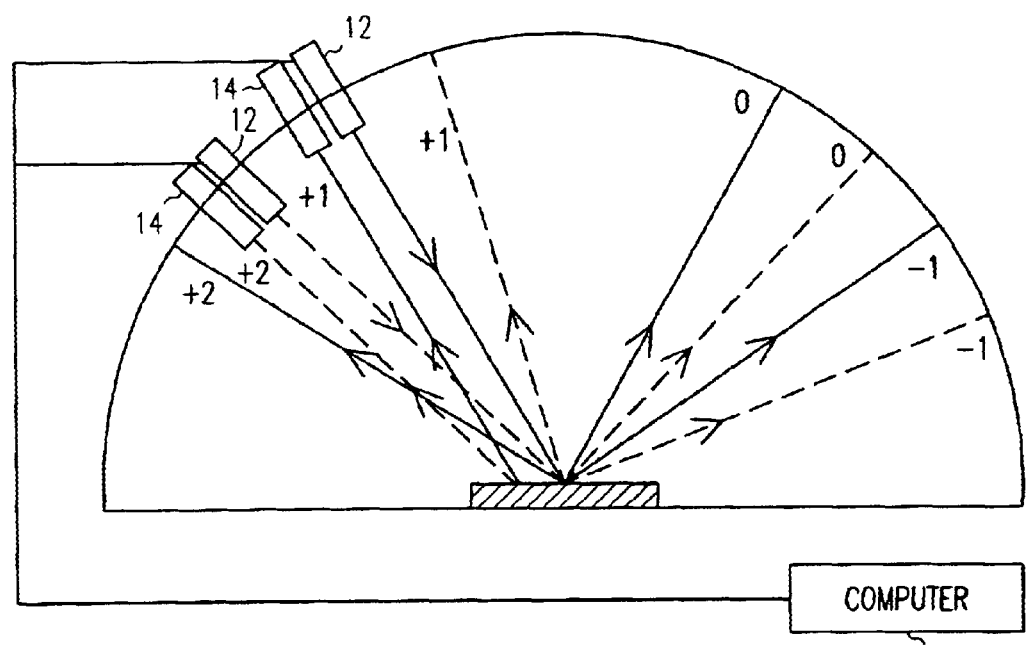

In another embodiment, multiple fixed laser/detector apparatuses 38 are positioned at the desired Bragg angles as shown in FIG. 3b below. Each apparatus 38 includes a light source 12 and a detector 14. This latter configuration appears to have some advantages over that shown in FIG. 3a, especially since there are no moving parts. The laser could operate at a fixed wavelength or be tunable to operate at multiple wavelengths. Moreover, since the desired diffracted order to be measured is anti-parallel to the incident wave, it may be difficult to separate between the incoming diffracted wave and the outgoing incident wave even in the presence of a beam splitter. One remedy would consist of placing the laser at an incident angle of $\theta_n \pm \Delta\theta$, where $\theta_n$ is the nth Bragg angle and $\Delta\theta$ is a small angle increment. As a result, even though the nth diffracted wave still lies close to the incident wave, it is no longer anti-parallel to it and successful separation between both beams is possible.

Figure 3C:
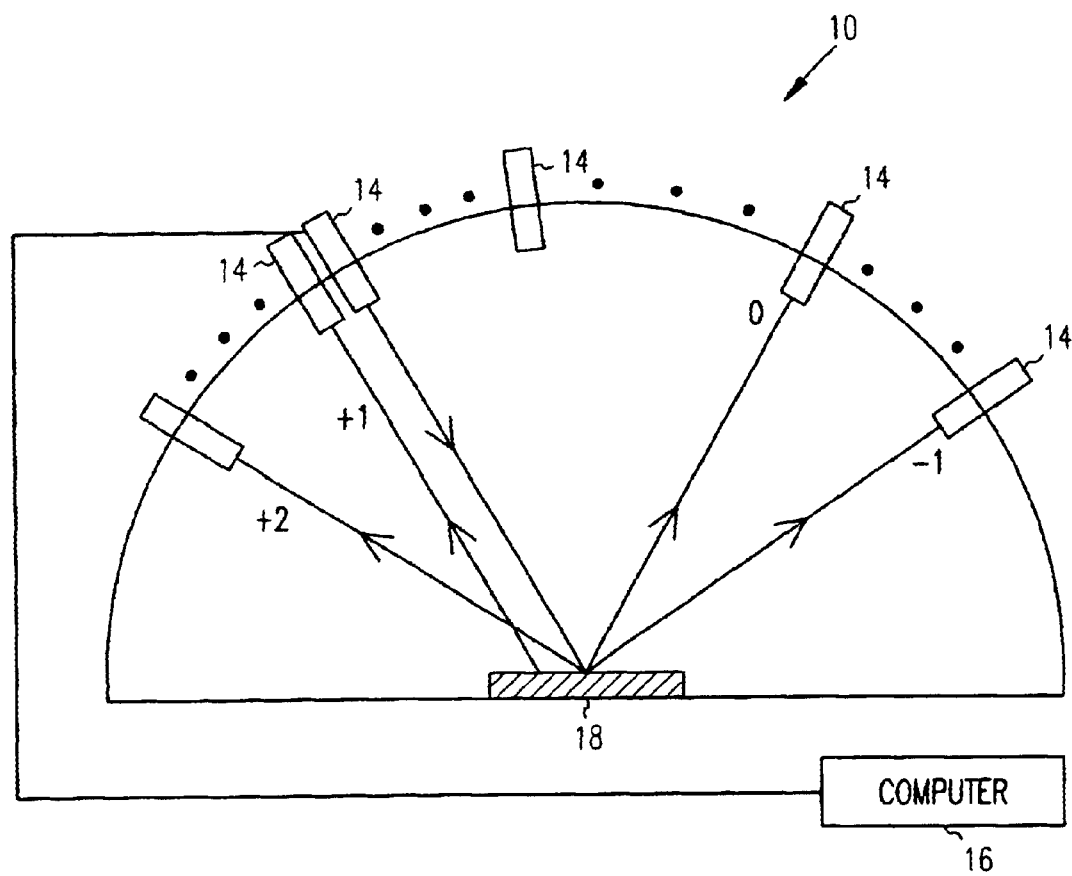

In yet another embodiment, such as is shown in FIG. 3c, a light source (not shown) is mounted such that it can be moved to a number of different positions within semicircular arc 32. A plurality of detectors 14 are fixedly mounted to positions along arc 32. In one such embodiment, detectors 14 are mounted in an approximately continuous fashion along arc 32. Such an approach can easily be adapted to changes in the anticipated Bragg angles due to changes in processing parameters.

Figure 4:
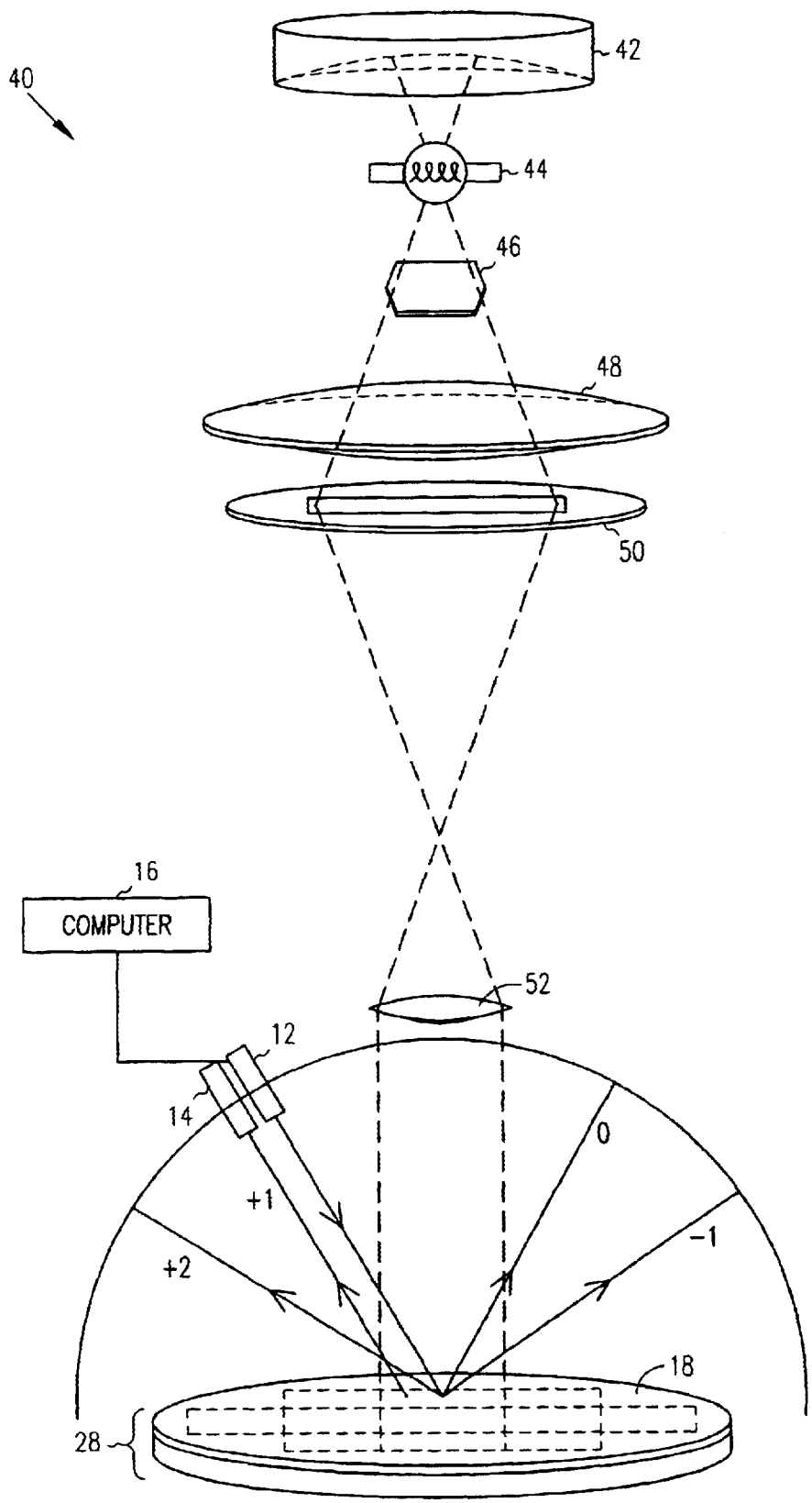
FIG. 4 illustrates a stepper which includes a latent image measurement system.

Latent image measurement system 10 can also be adapted to be part of the stepper or track so that it can be easily incorporated in the fab line. One embodiment of such a stepper is shown in FIG. 4. FIG. 4 shows a stepper 40 having an arc lamp 44, a mirror 42, a filter 46, a condenser lens system 48, an optical pattern transfer tool 50 and a lens reduction system 52. Light from arc lamp 44 is reflected from mirror 42 and passes through filter 46. Condenser lens system 48 focuses the light on optical pattern transfer tool 50 in order to transfer the pattern on tool 50 through reduction lens system 52 onto wafer 18. Stepper 40 also includes a light source 12 and a detector 14 connected to a computer 16. In one embodiment, light source 12 and detector 14 operate at a different wavelength from arc lamp 44 in order to reduce interaction with the photoresist coating wafer 18. In another embodiment, although the light source operates at a wavelength which causes a chemical change within the photoresist, the process is designed such that the added exposure is taken into account in determining exposure times and intensity.

Light source 12, detector 14 and computer 16 in stepper 40 cooperate to reconstruct an approximation to the latent image of a periodic structure on wafer 18. The reconstructed approximation can then be used to control, for instance, arc lamp 44 in order to more finely tune the changes desired in the photoresist.

Figure 5:
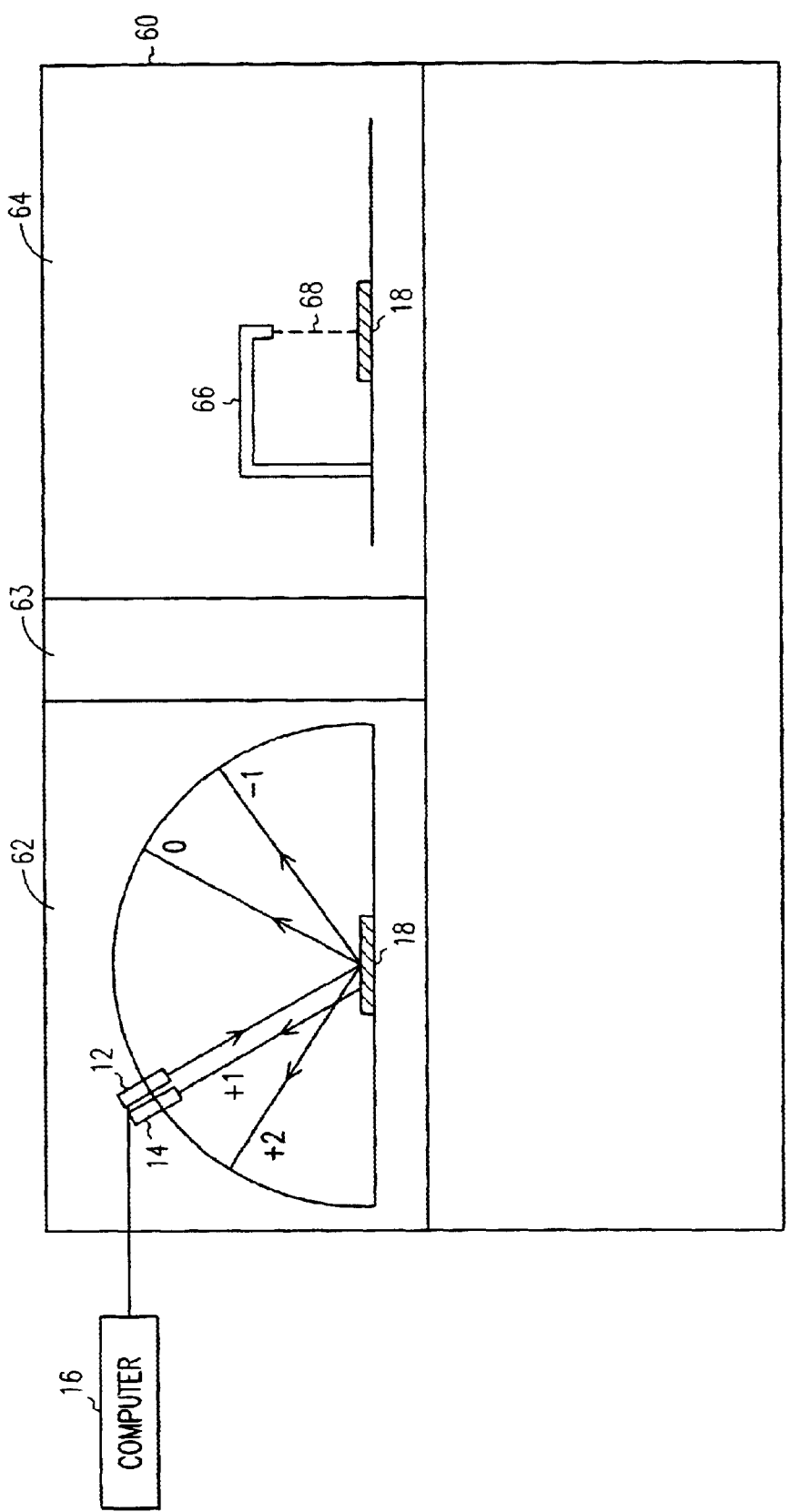
FIG. 5 illustrates a track which includes a latent image measurement system.

In a similar manner, latent image measurement system 10 can be adapted to a track 60 as is shown in FIG. 5. Track 60 includes a tomographic chamber 62, a bake chamber 63 and a development chamber 64. Tomographic chamber 62 includes a light source 12 and a detector 14 connected to a computer 16. Tomographic chamber 62 receives wafers 18 from a stepper upstream on the fab line and measures latent image formation as detailed above. As above, light source 12, detector 14 and computer 16 in track 60 cooperate to reconstruct an approximation to the latent image of a periodic structure on wafer 18. In one embodiment, light source 12 and detector 14 operate at a different wavelength from the light source used in the stepper upstream in order to reduce interaction with the photoresist coating wafer 18.

Bake chamber 63 includes a heating element used to heat wafer 18 to a desired temperature.

Development chamber 64 includes a faucet 66 used to spray developer fluid 68 on the surface of wafer 18. In one embodiment, both development chamber 64 and bake chamber 63 receive wafers 18 from tomographic chamber 62 and use data from computer 16 to control baking and developing of the exposed photoresist. In one such embodiment, the reconstructed approximation of the periodic structure is used to control the development process in development chamber 64 in order to more finely tune the changes desired in the photoresist.

Thus far, we have derived the FDT, under weakly scattering conditions, for two-dimensional structures consisting of latent image gratings on top of silicon substrate. A closed-form solution to the FDT was obtained by expanding the two-dimensional refractive index function, n(x,z), into its Fourier series representation. The FSR solution provided the necessary formulas to reconstruct the desired refractive indices. Very agreeable reconstructions are obtained from these formulas. In the following discussion, we expand our modeling to include more general cases, such as three-dimensional refractive index functions, n(x,y,z,)s, and the inclusion of multi layer dielectric surfaces between the photoresist and substrate.

Layered Media

Figure 6:
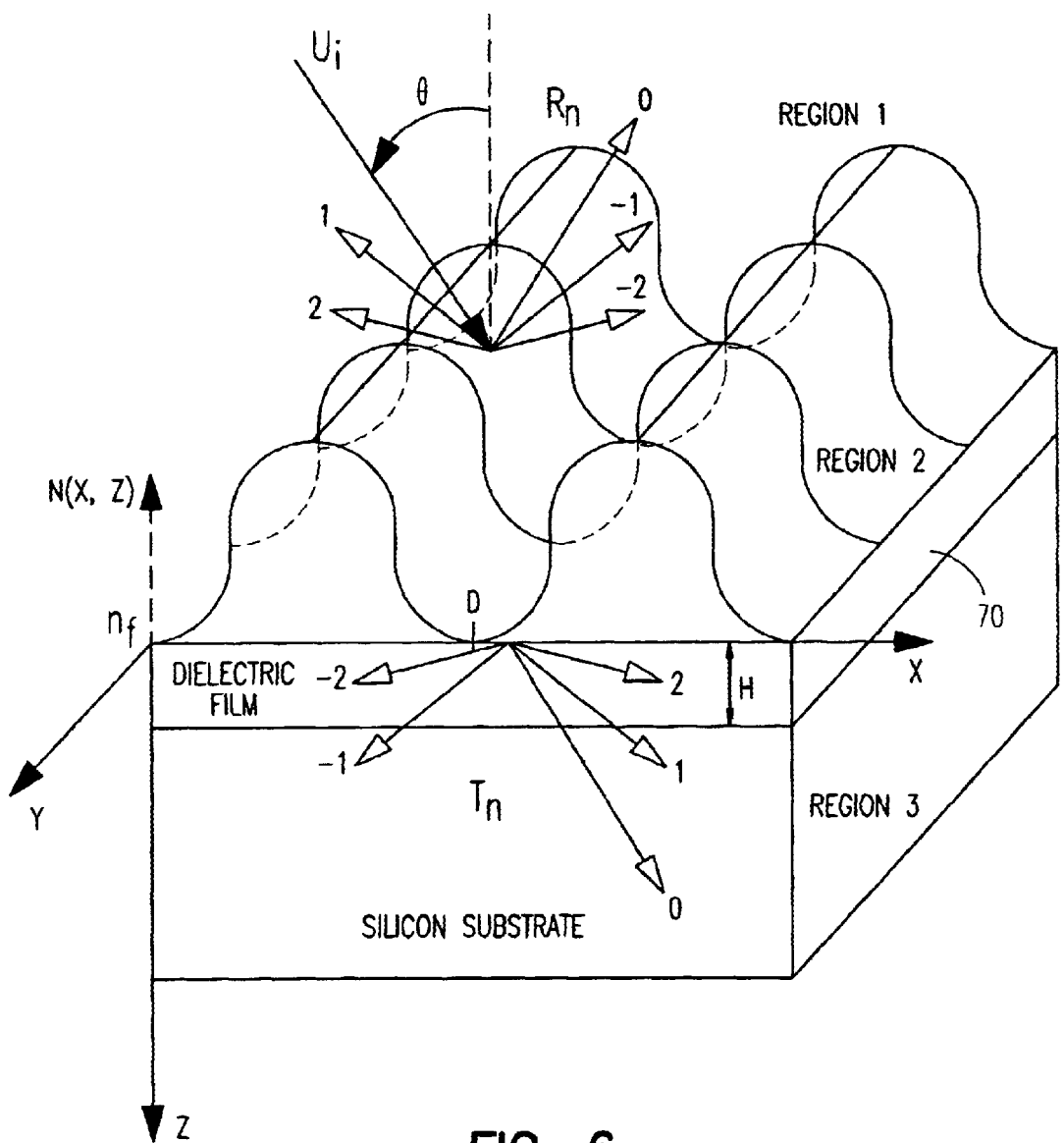
FIG. 6 is an illustration of a two-dimensional latent image grating formed over a dielectric film.

It is common practice in the semiconductor industry to include dielectric thin film layers between the photoresist and silicon substrate for various processing purposes. In the following discussion we address this issue by considering the case of one dielectric thin film layer only. It is shown that the single layer formulation is easily generalized to accommodate more than one dielectric layer. The geometry of the two-dimensional layered latent image grating treated in this work is shown in FIG. 6, which is very similar to the unlayered case shown in FIG. 2, except now we have included a dielectric thin film 70 of height H and refractive index $n_f$ between the photoresist and substrate.

Simulation of the effect of the dielectric layer on the above reconstruction technique shows that reasonable reconstructions were obtained to a film thickness of 0.02 $\mu$m. From the simulation parameters, it appears that the effects of dielectric film surfaces can be ignored as long as their total thickness, H, is less than or equal to the photoresist's thickness, W.

Figure 7:
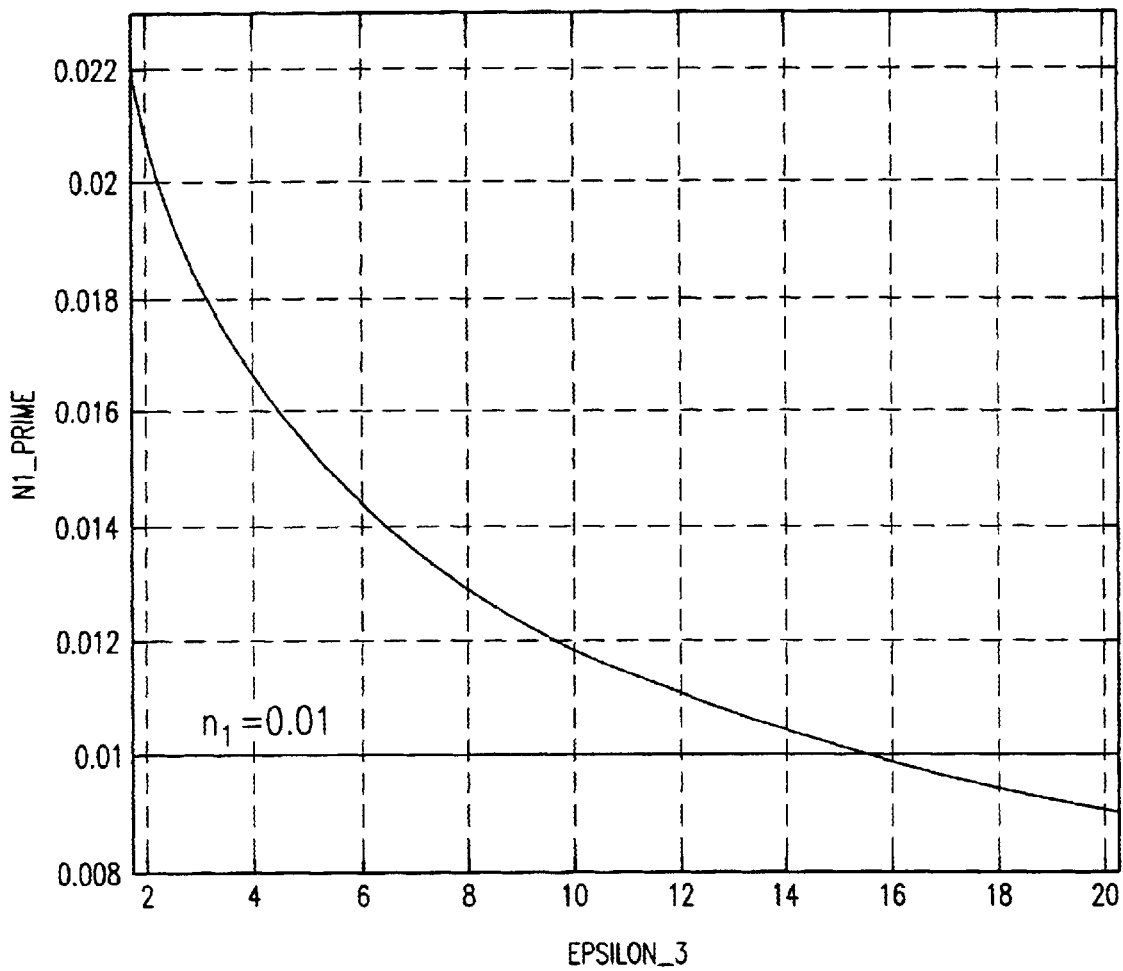
FIG. 7 is a plot of the reconstructed index of refraction for various level of permitivity in the substrate region.

An additional consideration, which arises from the layered media discussion and has not been addressed so far, is investigating the effects of the substrate material in region 3 on the reconstruction technique. In particular, as shown above, while the permittivity of the substrate region 3, $\epsilon_3$, was included into the formulation of transmission tomography, it was absent from the formulation of reflection tomography. This deficiency in the reflected case can be traced back to Rayleigh's expansion of the diffracted field in region 1, which does not incorporate $\epsilon_3$ into it. A different field expansion may be required to incorporate $\epsilon_3$ into the formulation. Nevertheless, in the following, we investigated the effects of varying the permittivity in region 3, $\epsilon_3$ on the quality of reconstructions, while keeping other parameters constant. In particular, in FIG. 7, we have plotted $n'_1$ as calculated by the FSR formulas for different $\epsilon_3$ values. For the sake of simplicity, we assumed that the imaginary part of the refractive index in region 3 was negligible, so that the permittivity, $\epsilon_3$ was purely real. We notice from FIG. 7, that agreeable reconstructions for $n'_1$ were obtained with an $\epsilon_3$ starting value of about 6. Below a value of 6, the reconstructions were inaccurate, which is of course due to the inability to incorporate the substrate's permittivity into the reflection tomography formulation. Overall though, reconstructions from reflected waves under first order approximations can be deemed insensitive into the substrate region 3.

Three-dimensional Refractive Index Functions

Figure 8:
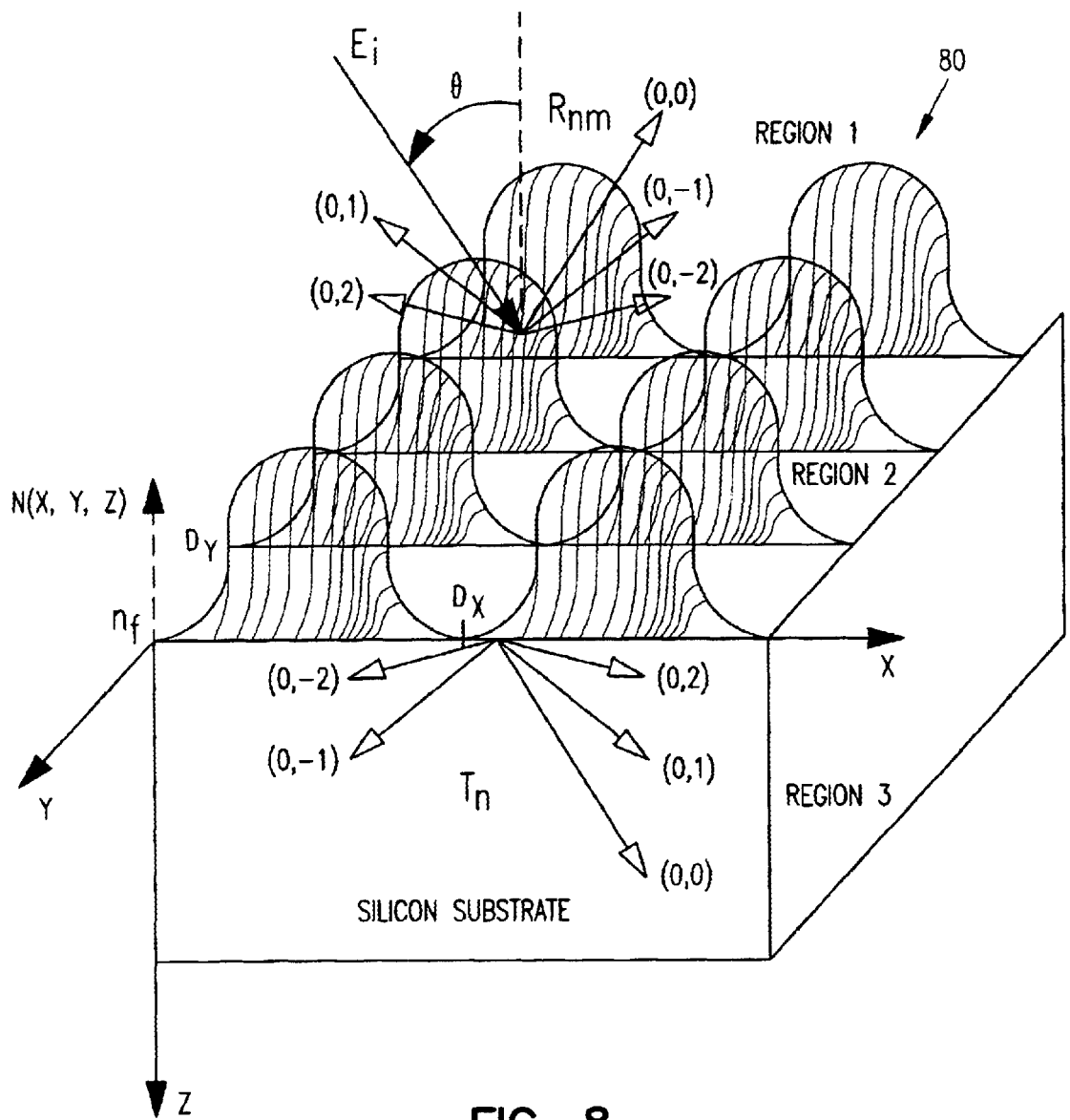
FIG. 8 is an illustration of a three-dimensional latent image grating.

The geometry of a three-dimensional latent image grating 80 is shown in FIG. 8. An electric field, $E_i$, obliquely incident on the grating, produces both forward diffracted (transmitted) waves in region 3 and backward diffracted (reflected) waves in region 1. The diffracted wave front in this case is two-dimensional along both the x and y directions. Region 1 is the input region with relative permittivity $\epsilon_1$. Region 2 contains the grating denoted by its three-dimensional periodic complex refractive index distribution, n(x,y,z), periods, $D_x$ and $D_y$ along the x and y directions respectively, and height, or thickness, W. Region 3 contains the silicon substrate with relative permittivity $\epsilon_3$.

Similar to Equation (5), the solution to the diffracted field in both regions 1 and 3 is still given by the general inhomogeneous wave equation $$\nabla^2 E_d(\vec{r}) + k_1^2 E_d(\vec{r}) = o(x,y,z) E(\vec{r}) \qquad (30)$$

Unlike the more comprehensive treatment given for the two-dimensional example above, in the following, we consider only the solution to the diffracted field in region 1, i.e., for reflected waves only, under the first Born approximation.

This leads to the following very important relation $$R_{nm} = \frac{1}{j4\pi D_x D_y} \frac{1}{k_{znm}} O_\tau(K_x, K_y, K_z). \qquad (31)$$

Equation (31) is the much sought FDT for reflection, for it relates the three-dimensional Fourier transform of the object function to the two-dimensional complex reflection coefficients. Therefore, from the complex reflection coefficients, $R_{nm}$, the Fourier transform of the object function in the ($K_x,K_y,K_z$) frequency domain is reconstructed as follows $$O_\tau(K_x,K_y,K_z) = j4\pi D_x D_y k_{znm} R_{nm}, \qquad (32)$$

or in intensity form $$|O_\tau(K_x, K_y, K_z)|^2 = |j4\pi D_x D_y k_{znm}|^2 DE_{1nm} \frac{k_{z0}}{k_{znm}} \qquad (33)$$

where $DE_{1nm}$ is the diffraction efficiency of $R_{nm}$ in region 1.

As mention earlier, equation (33) is ill-posed due to the discrepancy in its dimensionality. This is corrected by expanding the three-dimensional refractive index function, n(x,y,z), into its even periodic Fourier series, and by writing the object function o(x,y,z) in its exponential Fourier series expansion to obtain $$O_\tau(K_x, K_y, K_z) = \tag{34}$$

$$D_x D_y W \ \text{sinc}\left[\frac{K_z W}{2\pi}\right] \sum_{p=-2N}^{2N} \sum_{q=-2N}^{2N} O_{pq} \text{sinc}[n-p]\text{sinc}[m-q], \text{ or}$$

$$O_\tau(K_x, K_y, K_z) = D_x D_y W \ \text{sinc}\left[\frac{K_z W}{2\pi}\right] O_{nm}, \tag{35}$$

Hence, equating both (32) and (35) we obtain $$j4\pi k_{znm} R_{nm} = W \ \text{sinc}\left[\frac{K_z W}{2\pi}\right] O_{nm}, \tag{36}$$

Equation 36 defines the much sought FSR procedure for three-dimensional periodic structures, for it relates the two-dimensional exponential Fourier coefficients of the object function to the two-dimensional complex reflection coefficients. In addition, Equation (36) is well-posed because both its sides have now the same dimensions, as desired. Therefore, from the complex reflection coefficients, $R_{nm}$s, the object function, $o(x,y,z)$ is reconstructed as follows $$O_{nm} = \frac{j4\pi k_{znm}}{W^2 \text{sinc}^2\left[\frac{K_z W}{2\pi}\right]} R_{nm}, \tag{37}$$

or in intensity form $$|O_{nm}|^2 = \frac{16\pi^2 k_{znm} k_{z0}}{W \ \text{sinc}\left[\frac{K_z W}{2\pi}\right]} DE_{1nm}, \tag{38}$$

Since we are operating under weakly scattering conditions, we exclude specular reflection, i.e., (n=0, m=0), form the reconstruction process of Equations (37) and (38); weakly scattering really only applies to off-specular diffraction orders. Thus, in the following, we discuss recovering n(x, y, z) given $R_{nm}$s for $(n,m) \neq (0,0)$.

In the following, and for the sake of simplicity, we consider only the case N=1 while deriving reconstruction formulas. This treatment can be easily extended, at the expense of added algebraic complexities, to derive reconstruction formulas for higher order Ns. In particular for N=1 we have $$n(x, y, z) = \tag{39}$$

$$n_{00} + n_{01}\cos\left(\frac{2\pi y}{D_y}\right) + n_{10}\cos\left(\frac{2\pi x}{D_x}\right) + n_{11}\cos\left(\frac{2\pi x}{D_x}\right)\cos\left(\frac{2\pi y}{D_y}\right),$$

and we are interested in reconstructing the refractive index modulation values, $n_{01}$, $n_{10}$, and $n_{11}$. The derivation procedure is similar to the two-dimensional case and progresses as follows. Substituting Equation (39) into the object function expression, which is given by $$o(x,y,z) = k_1^2[1 - n^2(x,y,z)] \tag{40}$$

we obtain complex exponential Fourier coefficients, $O_{nm}$, as $$O_{22} = O_{-22} = O_{2-2} = O_{-2-2} = -k_1^2 \frac{n_{11}^2}{16} \tag{41}$$

-continued $$O_{21} = O_{-21} = O_{2-1} = O_{-2-1} = -k_1^2 \left(\frac{n_{10} n_{11}}{4}\right)$$

$$O_{12} = O_{-12} = O_{1-2} = O_{-1-2} = -k_1^2 \left(\frac{n_{01} n_{11}}{4}\right)$$

or in intensity form $$|O_{22}|^2 = k_1^4 \frac{n_{11}^4}{256} \tag{42}$$

$$|O_{21}|^2 = k_1^4 \frac{n_{10}^2 n_{11}^2}{16}$$

$$|O_{12}|^2 = k_1^4 \frac{n_{01}^2 n_{11}^2}{16}$$

Therefore, assuming the desired diffraction efficiencies are observable and measurable in region 1, and estimates of the periods, $D_x, D_y$ and thickness, W, are available, the intensities of the Fourier coefficients in (41) are calculated according to Equation (38). In particular, given $|O_{22}|^2$, $n_{11}$ is reconstructed as follows $$n_{11} = \sqrt[4]{\frac{256|O_{22}|^2}{k_1^4}}, \tag{43}$$

Moreover, given $|O_{21}|^2$, $|O_{12}|^2$, and $n_{11}$, $n_{10}$ and $n_{01}$ are reconstructed as follows $$n_{10} = \sqrt{\frac{16|O_{21}|^2}{k_1^4 n_{11}^2}} \tag{44}$$

$$n_{01} = \sqrt{\frac{16|O_{12}|^2}{k_1^4 n_{11}^2}}$$

Note that $n_{10}$ and $n_{01}$ could have been alternatively determined from $|O_{20}|^2$ and $|O_{02}|^2$, respectively. This nonuniqueness issue in determining the modulation refractive indices did not manifest itself for two-dimensional structures. In addition, as was the case for two-dimensional object functions, the remaining Fourier coefficients can be used to determine the average refractive index $n_{00}$ in a nonunique manner.

With continuous advancements in semiconductor technology, proper monitoring and control of features such as critical dimension (CDS) is of critical importance in the microelectronics industry for improving productivity yield and device reliability. This is especially relevant as CDS decrease into the 0.18 $\mu$m generation devices. By monitoring latent image formation inside a layer of photoresist, it is possible to infer crucial information about CDS prior to the development stage, thus avoiding one additional processing step. Otherwise, scanning electron microscopes (SEMs) would be used after development to measure CDS in a generally destructive manner, consequently establishing crude correlations between exposure conditions and developed CD pattern. Depending on the type of photoresists, successful CD control, prior to development, is usually performed during different fabrication processes, such as post exposure bake (PEB) for chemically amplified resists, silylation for surface imaging resists, and antireflecting (ARC) layers for conventional resists. As a particular example of these processes, the PEB process is performed on latent images prior to development in order to increase the chemical reaction rates. By monitoring latent image formation, it is possible to provide crucial control parameters for the PEB process, such as bake time and temperature, to achieve the necessary conditions required for the desired final developed CDS. The diffraction tomography technique described above nondestructively reconstructs the refractive index distribution in latent images during and/or after exposure but prior to development. This technique requires as input the diffracted field, complex or magnitude, from latent images generated by nonexposing light sources. The reconstruction formulas in turn produce at the output reconstructed versions of the latent images. Unlike other latent image monitoring techniques, this technique is able to quantitatively determine the refractive index distributions occurring inside photoresists.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A method of reconstructing an image of a structure having periodic variations in its index of refraction, the method comprising:

projecting electromagnetic waves onto the structure at an angle corresponding to a predetermined diffraction order;

measuring electromagnetic waves diffracted from the structure at that angle, wherein measuring includes determining a plurality of intensities $DE_{1(N+1)}$ through $DE_{1(2N)}$, wherein N is an integer greater than or equal to 1; and calculating a plurality of refractive terms $n_0$ through $n_N$, wherein calculating includes;

calculating refractive term $n_N$ as a function of $DE_{1(2N)}$;

calculating refractive term $n_{N-1}$ as a function of $n_N$ and $DE_{1(2N-1)}$; and calculating refractive term $n_1$ as a function of $DE_{1(N+1)}$ and of $n_2$ through $n_N$.

2. The method according to claim 1 wherein projecting electromagnetic waves includes positioning a laser to illuminate the structure at an angle where the angle is a Bragg incident angle.

3. A method of reconstructing a structure having periodic variations in index of refraction, the method comprising:

projecting electromagnetic waves onto the structure at an angle corresponding to a predetermined diffraction order;

measuring electromagnetic waves diffracted from the structure at that angle, wherein measuring includes determining a first and a second intensity;

calculating first and second exponential Fourier series coefficients as a function of the first and second intensities;

calculating a first refractive coefficient $n_1$ as a function of the first exponential Fourier coefficient; and calculating a second refractive coefficient $n_0$ as a function of the calculated first coefficient $n_1$ and the second exponential Fourier coefficient.

4. The method according to claim 3 wherein projecting electromagnetic waves includes positioning a laser to illuminate the structure where the angle is a Bragg incident angle.

5. The method according to claim 3 wherein measuring includes positioning a detector to measure backward diffracted waves at a Bragg angle.

6. A method of measuring latent image formation in photoresist by reconstruction of a latent image of a grating exposed in the photoresist, comprising:

illuminating the photoresist at an angle corresponding to a predetermined diffraction order;

measuring backward diffracted waves at that angle, wherein measuring includes determining a first and a second intensity;

calculating first and second exponential Fourier coefficients as a function of the first and second intensities;

calculating a first refractive coefficient $n_1$ as a function of the first exponential Fourier coefficient; and calculating a second refractive coefficient $n_0$ as a function of the first coefficient $n_1$ and the second exponential Fourier coefficient and reconstructing the image using the coefficients.

7. The method according to claim 6 wherein the angle is a Bragg incident angle.

8. The method according to claim 6 wherein measuring includes positioning a detector to measure backward diffracted waves at a Bragg angle.

9. Apparatus for monitoring latent image formation within an exposed undeveloped photoresist grating structure having periodic variations in index of refraction, comprising:

a light source for illuminating the grating structure at an incident angle corresponding to a predetermined diffraction order;

a detector positioned to measure light diffracted from the grating structure at an angle substantially equal to the incident angle; and a processor for quantitatively reconstructing a representation of a latent image of the grating structure as a function of the intensity of the light diffracted from the grating structure wherein the representation includes refractive coefficients calculated from exponential Fourier coefficients.

10. The apparatus according to claim 9 wherein the incident angle is at a Bragg incident angle.

11. The apparatus according to claim 9, wherein the detector is positioned at a Bragg angle to measure light backward diffracted from the structure.

12. The apparatus according to claim 11, wherein the apparatus further includes a second light source and a second detector, wherein the second light source and the second detector are positioned at a second Bragg angle.

13. The apparatus according to claim 9, wherein the apparatus further includes a motor connected to the light source and the detector.

14. The apparatus according to claim 9, wherein the apparatus further includes a second and a third detector approximately positioned at Bragg angles to the incident angle.

15. A stepper, comprising:

a fixture for receiving a wafer coated with a photoresist layer and a photomask for applying a periodic undeveloped, exposed grating pattern to the photoresist layer;

a first light source for illuminating the photoresist layer of the wafer through the photomask at a first incident angle corresponding to a predetermined diffraction order;

a second light source positioned to illuminate the pattern of the photoresist layer of the wafer at a second incident angle corresponding to a predetermined diffraction order, wherein the second angle is different from the first incident angle;

a detector positioned to measure light diffracted from the pattern of the photoresist layer of the wafer at the first and at the second incident angle;

a processor for quantitatively reconstructing a representation of a latent image of the periodic grating pattern of the photoresist layer, the latent image being represented as a function of the light diffracted from the pattern by calculating a plurality of refractive index terms as a function of exponential Fourier coefficients.

16. The apparatus according to claim 15, wherein the second incident angle is at a Bragg incident angle.

17. The apparatus according to claim 15, wherein the detector is positioned at a Bragg angle to measure light backward diffracted from the structure.

18. A track, comprising:

a bake chamber;

a development chamber;

a light source positioned to illuminate an exposed, undeveloped, latent image of a structure in a photoresist coating on a wafer, the structure having periodic variations of the index of refraction, the latent image illuminated at an incident angle corresponding to a predetermined diffraction order;

a detector positioned to measure light backward diffracted from the wafer at that angle; and a calculator for processing the measured light from the detector and reconstructing the quantitative latent image in the photoresist as a function of the light diffracted from the structure by calculating a plurality of refractive index terms using an exponential Fourier analysis.

19. The apparatus according to claim 18 wherein the incident angle is at a Bragg incident angle.

20. Apparatus for monitoring latent image formation within an exposed, undeveloped photoresist structure having periodic variations in index of refraction, comprising:

a light source for illuminating the structure at an incident angle corresponding to a predetermined diffraction order;

a detector positioned to measure light diffracted from the structure at that angle; and a processor for quantitatively reconstructing a representation of a latent image of the structure as a function of the intensity of light diffracted by the structure wherein the representation includes refractive coefficients calculated from exponential Fourier coefficients.

21. Apparatus for monitoring latent image formation in an exposed, undeveloped photoresist layer on a structure having periodic variations in index of refraction, comprising:

a light source for illuminating the layer at an incident angle corresponding to a predetermined diffraction order;

a detector positioned to measure light diffracted from the exposed, undeveloped photoresist layer at that angle; and a processor for quantitatively reconstructing a representation of the latent image by calculating a plurality of refractive index terms using an exponential Fourier analysis from the measured intensity of first and second diffraction orders.

22. Apparatus for monitoring latent image formation in a photoresist layer on a structure having periodic variations in index of refraction introduced by exposing the photoresist with an image of a grating, comprising:

a light source for illuminating an exposed but undeveloped photoresist layer at an incident angle corresponding to a predetermined diffraction order;

a detector positioned to measure light diffracted from the photoresist layer at that angle; and a processor for quantitatively reconstructing a representation of the latent image by calculating a plurality of refractive index terms using an exponential Fourier analysis from their first (+1) and second (+2) refracted diffraction orders at the Bragg angle.

23. A method of reconstructing an image of a structure having periodic variations in its index of refraction, the method comprising:

projecting electromagnetic waves onto the structure at a Bragg angle;

measuring electromagnetic waves diffracted from the structure at the Bragg angle, wherein measuring includes determining a plurality of intensities $DE_{1(N+1)}$ through $DE_{1(2N)}$, wherein N is an integer greater than or equal to 1; and calculating a plurality of refractive terms $n_0$ through $n_N$, wherein calculating includes:

calculating refractive term $n_N$ as a function of $DE_{1(2N)}$;

calculating refractive term $n_{N-1}$ as a function of $n_N$ and $DE_{1(2N-1)}$; and calculating refractive term $n_1$ as a function of $DE_{1(N+1)}$ and of $n_2$ through $n_N$.

24. A method of reconstructing a structure having periodic variations in index of refraction, the method comprising:

projecting electromagnetic waves onto the structure at a Bragg angle;

measuring electromagnetic waves diffracted from the structure at the Bragg angle, wherein measuring includes determining a first and a second intensity;

calculating first and second exponential Fourier series coefficients as a function of the first and second intensities;

calculating a first refractive coefficient $n_1$ as a function of the first exponential Fourier coefficient; and calculating a second refractive coefficient $n_0$ as a function of the calculated first coefficient $n_1$ and the second exponential Fourier coefficient.

25. A method of measuring latent image formation in photoresist by reconstruction of a latent image of a grating exposed in the photoresist, comprising:

illuminating the photoresist at a Bragg angle;

measuring backward diffracted waves at the Bragg angle, wherein measuring includes determining a first and a second intensity;

calculating first and second exponential Fourier coefficients as a function of the first and second intensities;

calculating a first refractive coefficient $n_1$ as a function of the first exponential Fourier coefficient; and calculating a second refractive coefficient $n_0$ as a function of the first coefficient $n_1$ and the second exponential Fourier coefficient thereby reconstructing the image.

26. Apparatus for monitoring latent image formation within an exposed but undeveloped photoresist structure having periodic variations in index of refraction, comprising:

a light source for illuminating the structure at a Bragg incident angle;

and a detector positioned to measure light diffracted from the structure at the Bragg angle; and a processor for quantitatively reconstructing a representation of a latent image of the structure as a function of the intensity of the light diffracted from the structure wherein the representation includes exponential Fourier Series refractive index coefficients.

27. A stepper, comprising:

a fixture for receiving a wafer coated with a photoresist layer and a photomask for applying a periodic grating pattern to the photoresist layer;

a first light source for illuminating the photoresist layer of the wafer through the photomask at a first incident angle to apply a latent image of the grating to the layer;

a second light source positioned to illuminate the undeveloped pattern of the photoresist layer of the wafer at a second incident angle which is a Bragg angle, wherein the second angle is different from the first incident angle;

a detector positioned to measure light from the second light source diffracted from the pattern of the photoresist layer of the wafer at the Bragg angle;

a processor for quantitatively reconstructing a representation of a latent image of the periodic grating pattern of the undeveloped photoresist layer, the latent image being represented as a function of the light diffracted from the pattern by calculating a plurality of refractive index terms as a function of the exponential Fourier coefficients.

28. A track, comprising:

a bake chamber;

a development chamber;

a light source positioned to illuminate a latent image of a structure in a photoresist coating on a wafer, the structure having periodic variations of the index of refraction, the latent image illuminated at an incident angle which is a Bragg angle;

a detector positioned to measure light backward diffracted from the wafer at the Bragg angle; and a calculator for processing the measured light from the detector and reconstructing the quantitative latent image in the photoresist as a function of the light diffracted from the structure by calculating a plurality of refractive index terms using an exponential Fourier analysis from the +2 and +1 diffraction efficiencies at their respective Bragg angles.

29. Apparatus for monitoring latent image formation within an undeveloped photoresist structure having periodic variations in index of refraction, comprising:

a light source for illuminating the structure at an incident angle which is a Bragg angle;

a detector positioned to measure light diffracted from the structure at the Bragg angle; and a processor for quantitatively reconstructing a representation of a latent image of the structure as a function of the intensity of light diffracted by the structure by calculating a plurality of refractive index terms using an exponential Fourier analysis wherein the representation includes inverse diffraction coefficients.

30. Apparatus for monitoring latent image formation within an undeveloped photoresist structure having periodic variations in index of refraction, comprising:

a light source for illuminating the structure at an incident angle which is a Bragg angle;

a detector positioned to measure light backward diffracted from the structure at the Bragg angle; and a processor for quantitatively reconstructing a representation of the latent image by calculating plurality of refractive index terms using an exponential Fourier analysis to obtain the refractive index distribution of latent images.

31. Apparatus for monitoring latent image formation within an undeveloped photoresist structure having periodic variations in index of refraction, comprising:

a light source for illuminating the structure at a Bragg incident angle;

a detector positioned to measure light diffracted from the structure at the Bragg angle; and a processor for quantitatively reconstructing a representation of the latent image by calculating plurality of refractive index terms using an exponential Fourier analysis to obtain the refractive index distribution of latent images from their first (+1) and second (+2) refracted diffraction orders at the Bragg angle using.

* * * * *

UNITED STATES PATENT AND TRADEMARK OFFICE
CERTIFICATE OF CORRECTION

PATENT NO.     : 6,658,144 B1
DATED          : December 2, 2003
INVENTOR(S)    : Hatab It is certified that error appears in the above-identified patent and that said Letters Patent is hereby corrected as shown below:

Title page,
Item [56], References Cited, OTHER PUBLICATIONS, "Garcia, N., et al." reference, delete "18924)" and insert -- 18 (24) --, therefor.
"Steiglitz, K., et al.," reference, delete "Accoustics" and insert -- Acoustics --, therefor.
"Wolf, E., et al.," reference, delete "dtermination" and insert -- determination --, therefor.

Column 5,
Line 42, delete "," after "z".
Line 44, in Equation (7), insert -- ; -- after "0(x, z)".

Column 10,
Line 39, delete "$DE_{1(N-1)}$ -- and insert -- $DE_{1(N+1)}$ --, therefor.

Column 11,
Line 22, delete ";" and insert -- , --, therefor.

Column 13,
Line 30, delete "," after "z".

Column 15,
Line 26, in Equation (37), delete "$W^2$ $sinc^2$" and insert -- W sinc --, therefor.
Line 33, in Equation (38), delete "W sinc" and insert -- $W^2$ $sinc^2$ --, therefor.

Column 17,
Line 37, delete ";" and insert -- : --, therefor.

Signed and Sealed this

Eighteenth Day of May, 2004

JON W. DUDAS
*Acting Director of the United States Patent and Trademark Office*